United States Patent [19]

Kramer et al.

[11] Patent Number: 5,405,362
[45] Date of Patent: Apr. 11, 1995

[54] INTERACTIVE EXTERNAL DEFIBRILLATION AND DRUG INJECTION SYSTEM

[75] Inventors: George C. Kramer; Joel P. Jenkinson, both of Galveston, Tex.

[73] Assignee: The Board of Regents for the University of Texas System, Tex.

[21] Appl. No.: 170,065

[22] Filed: Dec. 20, 1993

Related U.S. Application Data

[60] Continuation-in-part of Ser. No. 958,279, Oct. 8, 1992, Pat. No. 5,271,744, which is a division of Ser. No. 692,674, Apr. 29, 1991, Pat. No. 5,176,643.

[51] Int. Cl.$^6$ ............................................. A61N 1/39
[52] U.S. Cl. .......................................... 607/5; 607/3; 128/697
[58] Field of Search ................... 607/3, 4, 5, 115, 119, 607/120, 127; 128/696, 697, 705, 709

[56] References Cited

U.S. PATENT DOCUMENTS

| | | |
|---|---|---|
| 2,426,535 | 8/1947 | Turkel . |
| 2,773,500 | 12/1956 | Young . |
| 3,396,726 | 8/1968 | Sarnoff . |
| 3,651,806 | 3/1972 | Hirshberg . |
| 3,712,301 | 1/1973 | Sarnoff . |
| 3,750,667 | 8/1973 | Pshenichny et al. . |
| 3,882,863 | 5/1975 | Sarnoff et al. . |
| 3,923,060 | 12/1975 | Ellinwood, Jr. . |
| 4,146,029 | 3/1979 | Ellinwood, Jr. . |
| 4,280,494 | 7/1981 | Cosgrove, Jr. et al. . |
| 4,619,265 | 10/1986 | Morgan et al. . |
| 4,880,014 | 11/1989 | Zarowitz et al. . |
| 4,919,144 | 4/1990 | Vandehey . |
| 5,078,134 | 1/1992 | Heilman et al. . |
| 5,086,772 | 2/1992 | Larnard et al. . |
| 5,087,243 | 2/1992 | Avitall . |
| 5,154,182 | 10/1992 | Moaddeb ............................ 607/129 |
| 5,156,148 | 10/1992 | Cohen . |
| 5,176,643 | 1/1993 | Kramer et al. . |
| 5,255,693 | 10/1993 | Dutcher et al. ...................... 607/120 |
| 5,324,324 | 6/1994 | Vachon et al. ...................... 607/120 |

OTHER PUBLICATIONS

Tocantins, L. M. and O'Neill, J. F., "Infusions of Blood and Other Fluids into the General Circulation Via the Bone Marrow," Surg. Genecol. Obstet., 73, 281–287 (1941).

Turkel, H. and Bethell, F. H., "A New and Simple Instrument for Administration of Fluids Through Bone Marrow," War Medicine, 222–225 (1944).

Glaeser, P. W. and Losek, J. D. "Intraosseous Needles: New and Improved," 38 Pediat. Emerg. Care. 4, 135–136 (1989).

Sacchetti, A. D., Linkenheimer, R., Lieberman, M., Haviland, P., Kryszozak, L. B., "Intraosseous Drug Administration: Successful Resuscitation from Asystole, Pediat. Emerg. Care", 5, 97–98 (1989).

Halvorsen, L., Bay, B. K., Perron, P. R., Gunter, R. A., Holcroft, J. W., Blaisdell, F. W., Kramer, G. C., "Evaluation of an Intraosseous Infusion Device for the Resuscitation of Hypovolemic Shock," J. Traum., 30, 652–659 (1990).

Laerdal Heartstart 3000 Operating Instruction provided by Laerdal Medical Corp.

Update to Heartstart 3000 Operating Instructions.

*Primary Examiner*—George Manuel
*Attorney, Agent, or Firm*—Rosenblatt & Associates

[57] ABSTRACT

This invention involves an interactive external defibrillation and drug injection system for use by a human operator for treating cardiac conditions in a patient, particularly in an out-of-hospital or pre-hospital environment. The present invention may also be used within hospitals as well as where intravenous (IV) access has not been established. More specifically, this invention comprises measuring devices capable of measuring and monitoring various physiological indicators in a patient and an expert system capable of analyzing the measured data and making recommendations to an operator for treatment of the patient using any combination of defibrillation, cardioversion, transcutaneous pacing, or vascular drug delivery via intraosseous drug injection. This invention is designed to enable first responders to cardiac emergencies to provide care up to the standard of at least the beginning stages of Advanced Cardiac Life Support (ACLS).

25 Claims, 18 Drawing Sheets

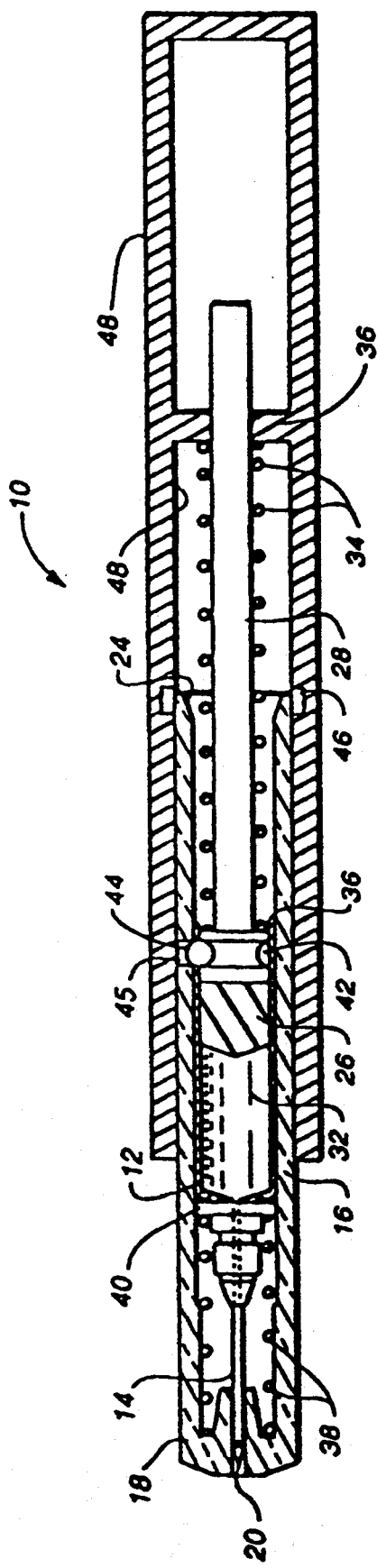
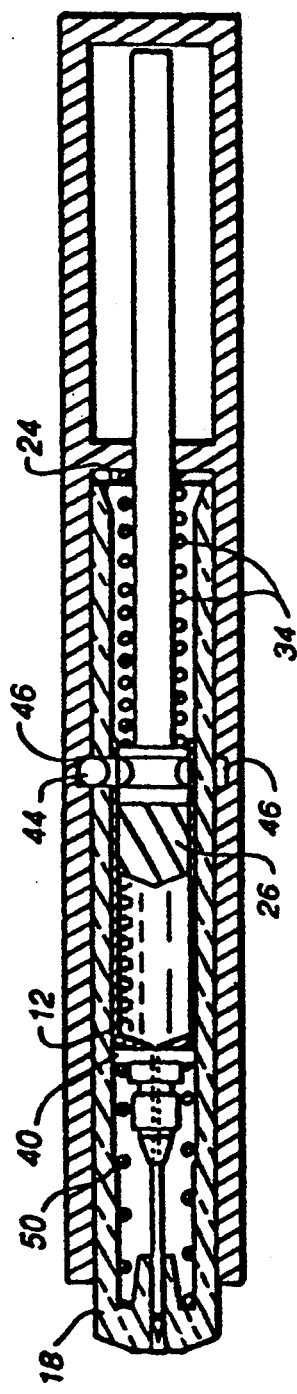
FIG._1
FIG._2

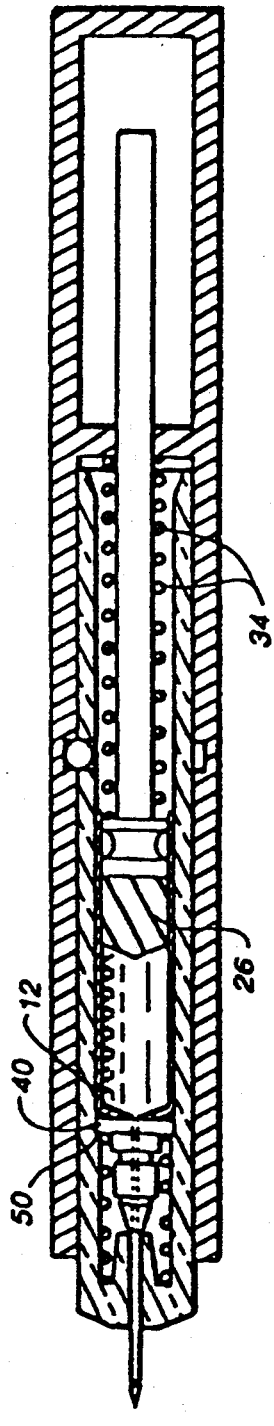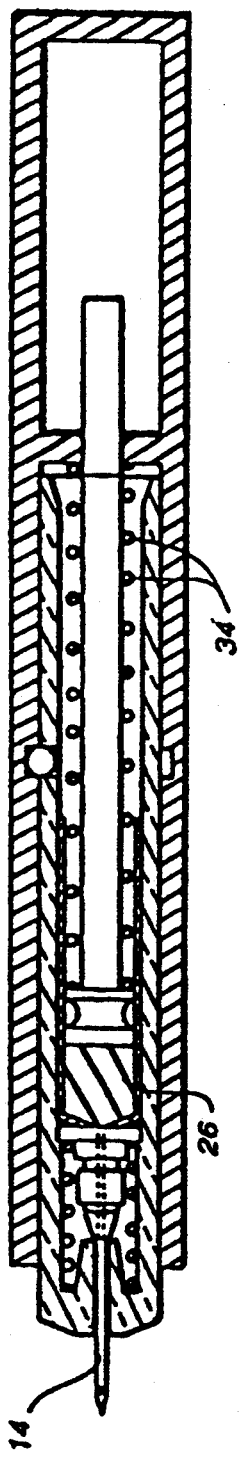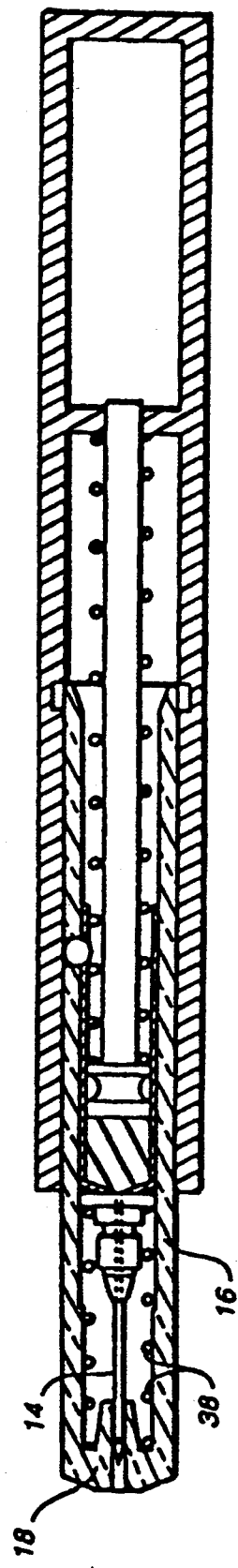

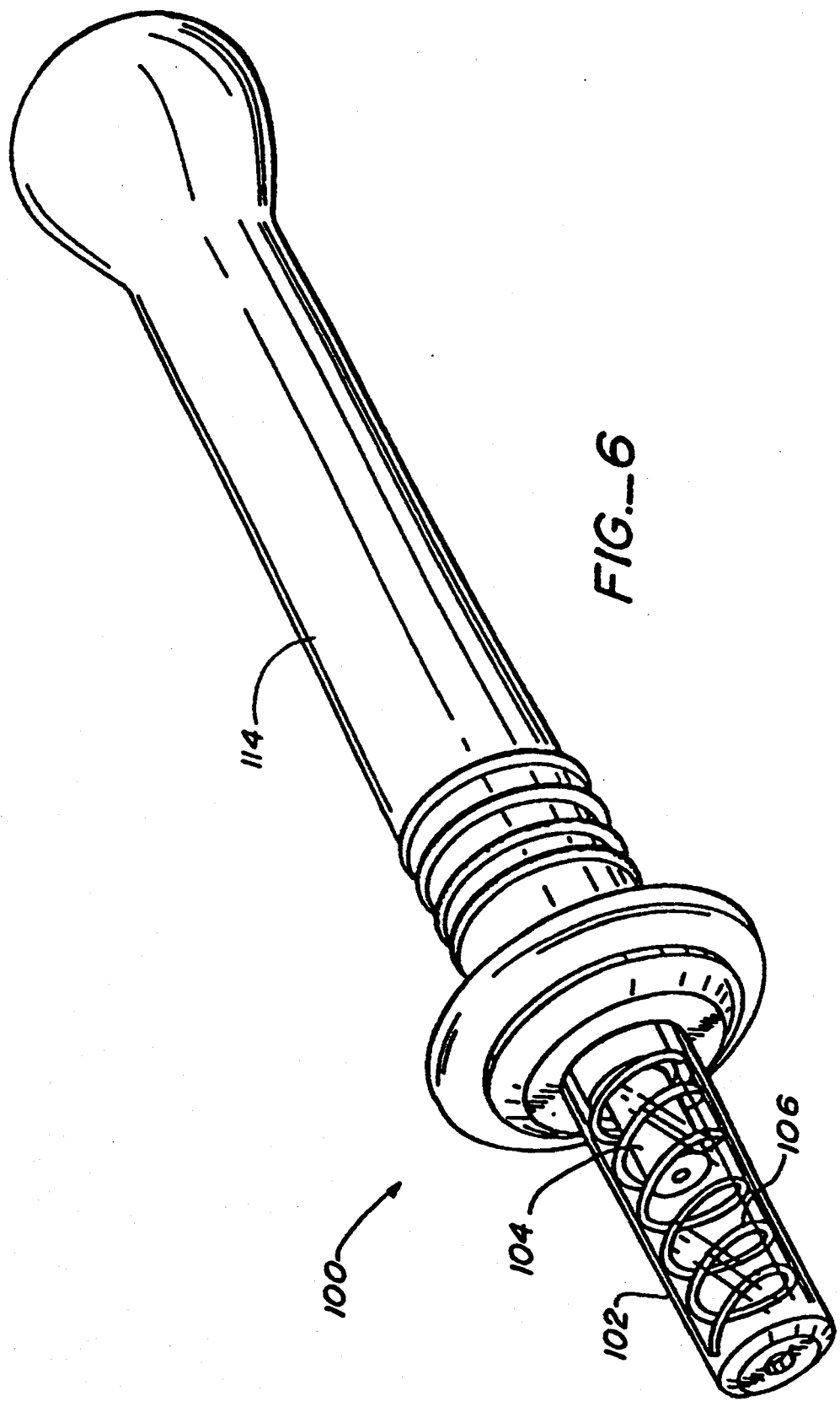
FIG._6

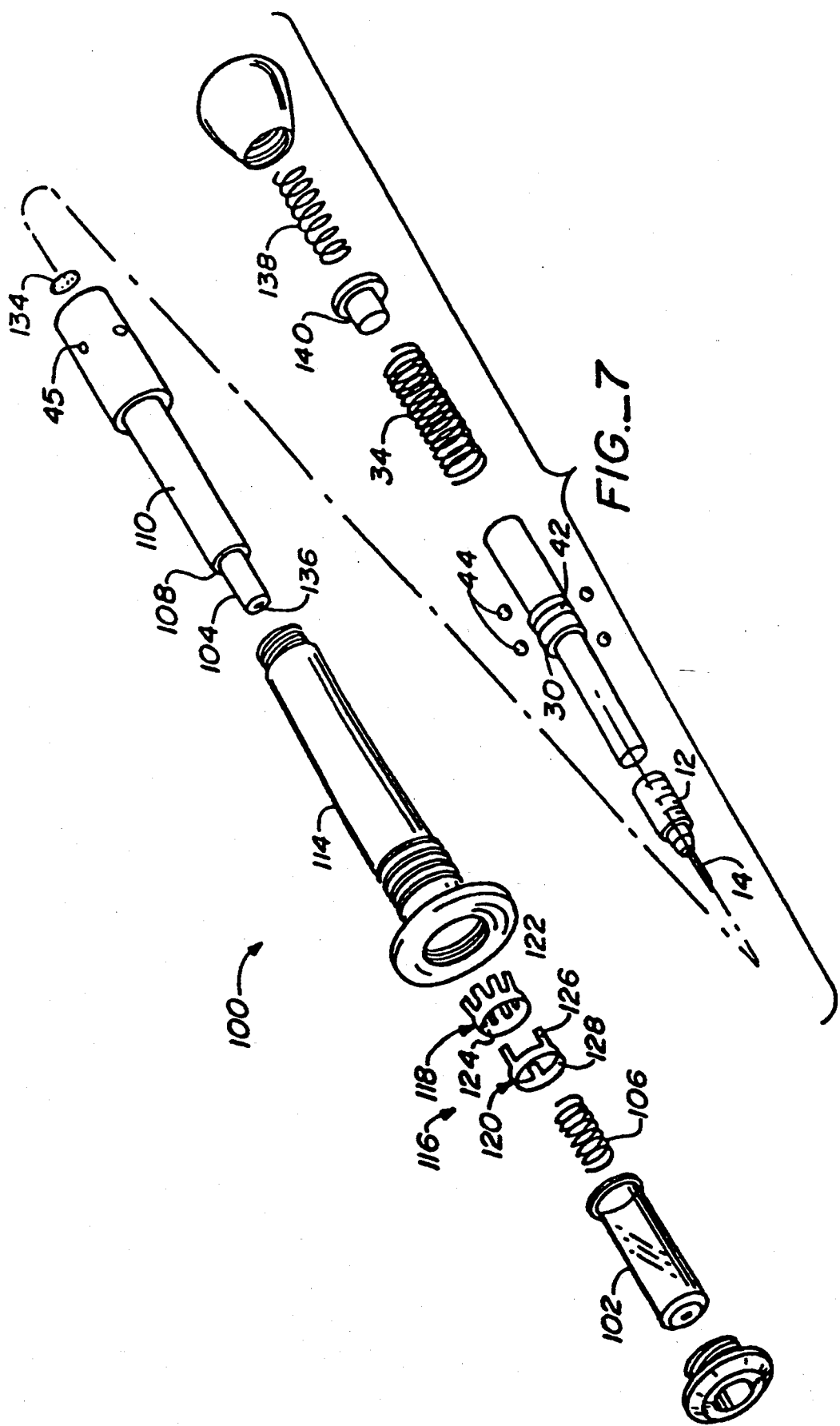

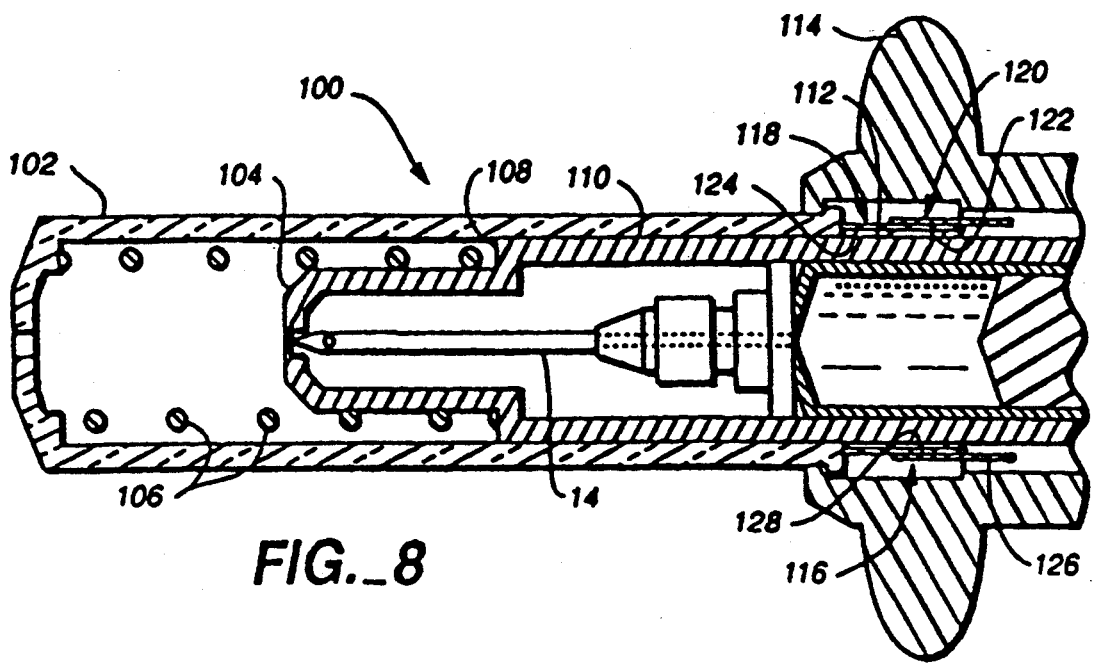
FIG._8
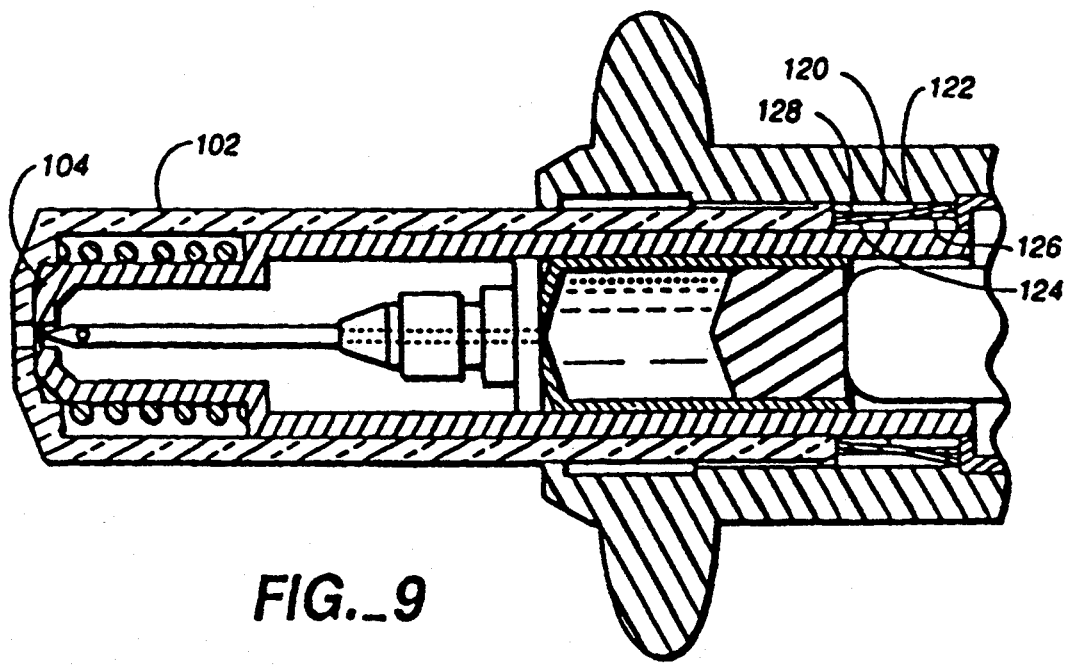
FIG._9

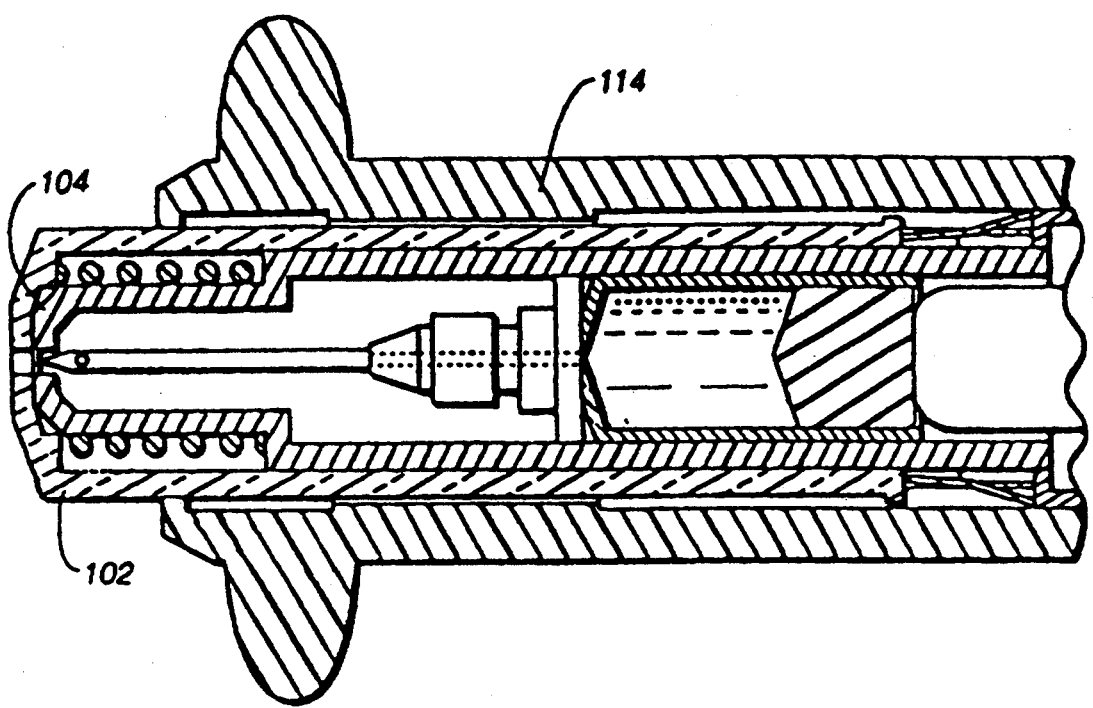
FIG._10

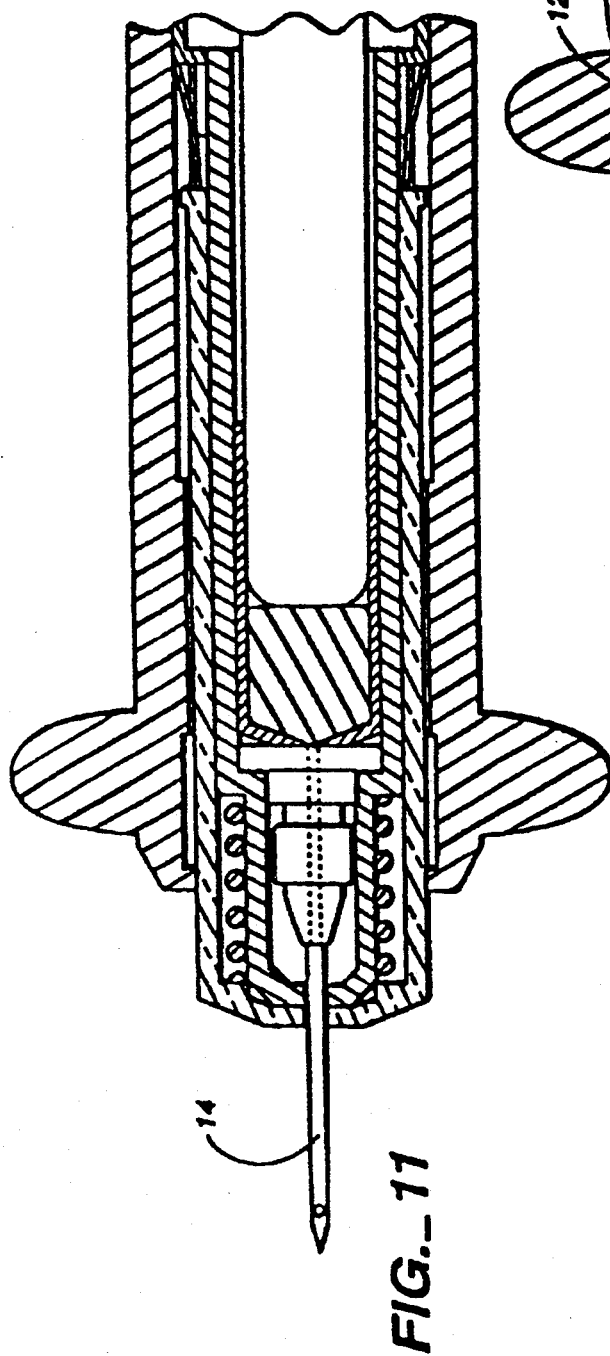
FIG._11
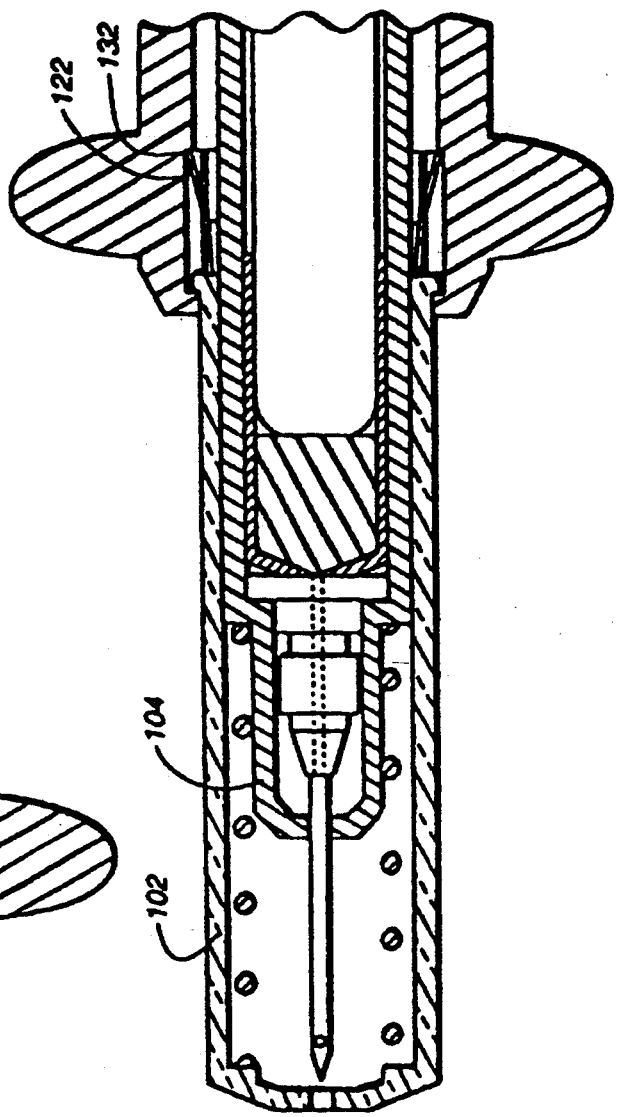
FIG._12

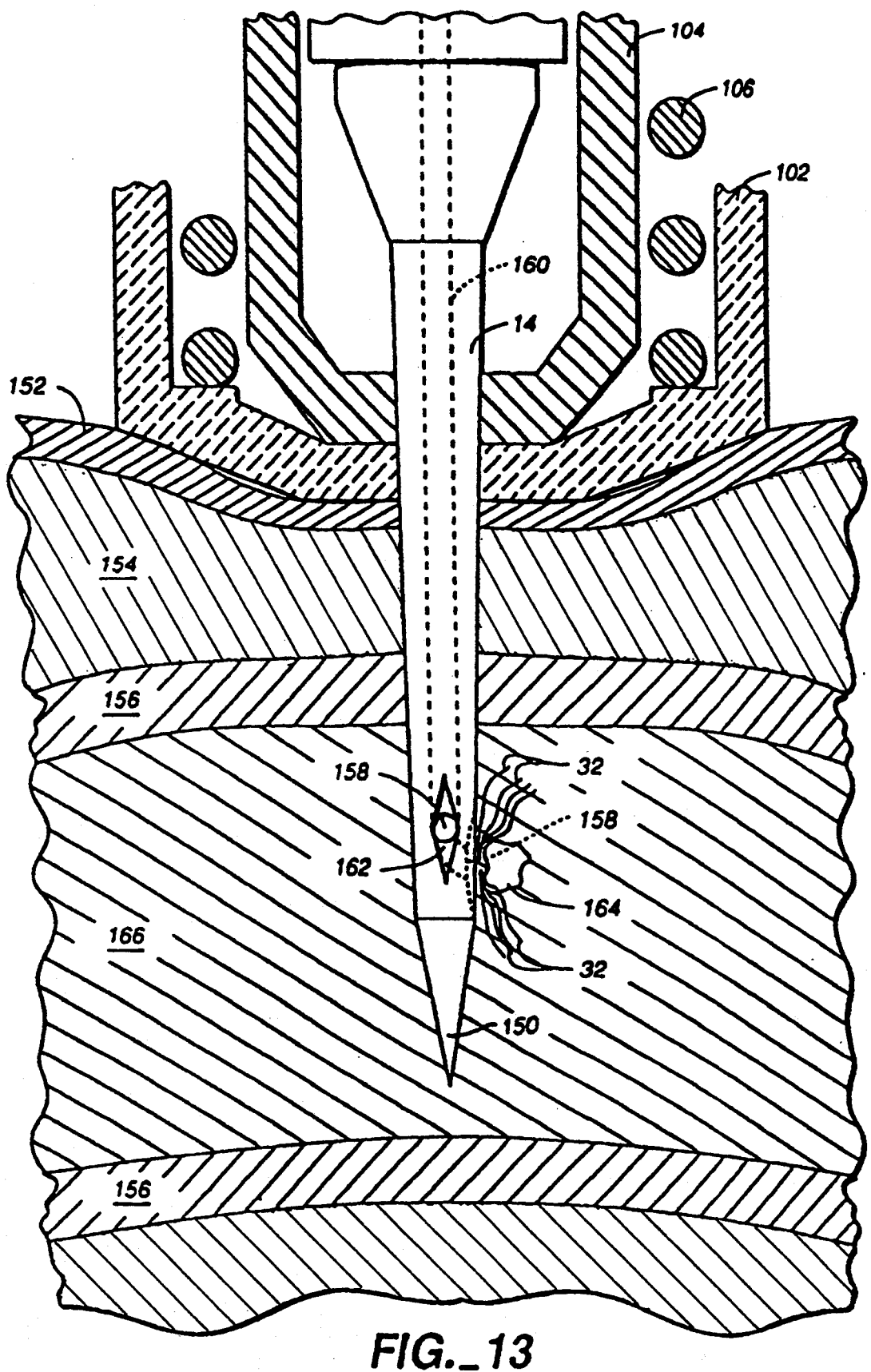
FIG._13

Analysis/Diagnosis

Ventricular Fibrillation/Ventricular Tachycardia

Pulseless Electrical Activity
(Electromechanical Dissociation)

Asystole

Acute Myocardial Infarction

Bradycardia

Tachycardia

Tachycardia, heart rate < 150 beats/minute

Hypotension / Shock / Acute Pulmonary Edema

INTERACTIVE EXTERNAL DEFIBRILLATION AND DRUG INJECTION SYSTEM

RELATED APPLICATION

This application is a continuation-in-part of application Ser. No. 07/958,279, filed on Oct. 8, 1992, now U.S. Pat. No. 5,271,744, which is a divisional application of application Ser. No. 07/692,674, filed on Apr. 29, 1991, and which issued as U.S. Pat. No. 5,176,643 on Jan. 5, 1993.

BACKGROUND OF THE INVENTION

1. Field of the Invention

This invention involves an interactive external defibrillation and drug injection system for use by a human operator for treating cardiac conditions in a patient, particularly in an out-of-hospital or pre-hospital environment. The present invention may also be used within hospitals as well, particularly where intravenous (IV) access has not been established. More specifically, this invention comprises devices capable of measuring and monitoring various physiological indicators in a patient and an expert system capable of analyzing the measured data and making recommendations to an operator for treatment of the patient using any combination of defibrillation, cardioversion, transcutaneous pacing, or intraosseous drug injection. This invention is designed to enable first responders to cardiac emergencies to provide care up to the standard of at least the beginning stages of Advanced Cardiac Life Support (ACLS).

2. Description of the Prior Art

Patients experiencing cardiac emergencies need immediate care. Survival rates for patients experiencing a cardiac emergency improve with early delivery of ACLS care. Defibrillation and the initiation of drug therapies are important components of ACLS. Unfortunately, beneficial drug therapies may be delayed by factors such as delays between the time of arrival of skilled paramedics or other advanced care providers qualified to initiate drug therapies; delays resulting from transportation of a patient to a hospital or other facility where drug therapy may be initiated; and difficulty or failure to establish IV access to a patient experiencing a cardiac emergency.

Treatment of cardiac emergencies may encompass cardiopulmonary resuscitation (CPR), cardioversion, defibrillation, transcutaneous pacing, and/or drug delivery via intraosseous injection. First responders to medical emergencies are frequently not physicians. Such first responders lack the training to make an independent evaluation regarding treatment of the patient with cardioversion, defibrillation, transcutaneous pacing, or drugs. Delays in administering such treatment can result in brain damage or death to the patient.

Prior art defibrillators include microprocessor controlled or "smart" defibrillators comprising algorithms or expert systems capable of receiving and analyzing physiological data from a patient and making a decision or recommendation as to the type of corrective action that should be administered. One type of smart defibrillator is disclosed in U.S. Pat. No. 4,619,265 to Morgan, et al. Morgan discloses an interactive portable smart defibrillator which processes physiological data from the patient and then sends messages or "prompts" to an operator, allowing the human operator to make the final decision regarding the delivery of defibrillation therapy. The device disclosed in Morgan is limited to treatment of the patient with a defibrillator. As explained above, a patient experiencing an emergency cardiac condition often requires drug delivery in addition to defibrillation or cardioversion.

Another type of smart defibrillator is the Heartstart ® 3000, manufactured by Laerdal Medical Corporation of Armonk, N.Y. Use of the Heartstart ® 3000 is contraindicated where the patient is conscious or breathing or where the patient has a pulse or a pacemaker. In general, consciousness, breathing, pulse, and pacemaker are contraindications precluding the use of automatic external defibrillators of the prior art. Patients in need of emergency cardiac care often exhibit one or more of these contraindications.

Another type of smart defibrillator is disclosed in U.S. Pat. No. 5,156,148 to Cohen. The system disclosed in Cohen comprises a central processing unit (CPU) that controls drug delivery devices, cardioverting apparatus, defibrillating apparatus, pacers, and heart assist pumps. However, the system disclosed in Cohen must be attached or implanted into the patient with vascular access devices in place. This presupposes that a cardiac emergency is likely. Such a system would likely be used in intensive care unit or for a very select group of very sick patients. Unfortunately, many, if not most, cardiac emergencies are unexpected and it is unlikely that such system would be in place with pre-existing vascular access for drug delivery.

A system of the type disclosed in Cohen does not require the presence of a physician for its operation, nor does it allow for human intervention in the treatment process. The system disclosed in Cohen is an automatic system where the machine or CPU makes a decision on the treatment to be administered and then administers such treatment without allowing for human input or intervention. The absence of human input or intervention from the operation of the system disclosed in Cohen raises ethical and legal concerns which may limit the application or acceptance of such a system.

There is a critical need for better and more rapid methods of vascular delivery of drugs. The development of new, life saving drugs and better knowledge of how specific drugs work has established that many drugs can prevent death or reduce morbidity if given in a timely manner. Unfortunately, most drugs need to be infused directly into the blood of the general circulation to be effective, and this is not always easily accomplished. Vascular injections and cannulations are procedures requiring professional skills and training that are usually only possessed by doctors, nurses and paramedics. Even these professionals have a significant failure rate and generate time delays for drug delivery in emergency conditions, when veins are often collapsed due to low blood pressure, and several procedures need to be accomplished as soon as possible. Many other professionals and lay personnel, such as flight attendants, police, life guards and teachers, are trained in advanced first aid and CPR, but cannot deliver drugs, due to lack of an effective method that does not require more medical training. Clearly, there is a need for a simple, better and more rapid means of drug delivery to aid both skilled professionals and para-professionals to expand the utility of life saving drugs.

It has long been known that the marrow sinuses of bones are virtual non-collapsible veins. Fluids and drugs have been shown to enter the central circulation after intraosseous (IO) infusions as rapidly or even more rapidly than peripheral vein infusions. This IO method can be used to deliver drugs via the long leg bones, the sternum, or other bones.

Many special needles and devices have been made both to sample marrow and to infuse fluids into the marrow. All of these needles require substantial training and skill for their correct and safe use and take several seconds to minutes to use them properly. Examples of such prior art devices are disclosed in U.S. Pat. Nos. 2,426,535, issued Aug. 26, 1947 to Turkel; 2,773,500, issued Jan. 26, 1955 to Young; 3,750,667, issued Aug. 7, 1973 to Pshenichny et al.; 4,969,870, issued Nov. 13, 1990 to Kramer et al., and in the following articles: Tocantins, L. M. and O'Neill, J. F., "Infusion of Blood and Other Fluids into the General Circulation Via the Bone Marrow," Surg. Gynecol. Obstet., 73, 281-287 (1941); Turkel, H. and Bethell, F. H., "A New and Simple Instrument for Administration of Fluids Through Bone Marrow," War Medicine, 5, 222-225 (1944); Glaeser, P. W. and Losek, J. D. "Intraosseous Needles: New and Improved," 38 Pediat. Emerg. Care. 4, 135-136 (1989); Sacchetti, A. D., Linkenheimer, R., Lieberman, M., Haviland, P., Kryszozak, L. B., "Intraosseous Drug Administration: Successful Resuscitation from Asystole," Pediat. Emerg. Care, 5, 97-98 (1989); Halvorsen, L., Bay, B. K., Perron, P. R., Gunther, R. A., Holcroft, J. W., Blaisdell, F. W., Kramer, G. C., "Evaluation of an Intraosseous Infusion Device for the Resuscitation of Hypovolemic Shock," J. Traum., 30, 652-659 (1990). The above references describe manually inserted needles and techniques which require skill and training for proper use and necessitate many seconds to minutes in use. An automated needle system for delivery of drugs into the marrow would have great utility.

A variety of auto-injection syringes for intramuscular or subcutaneous injections are also known in the art. Examples of such syringes are disclosed in the following U.S. Pat. Nos.: 3,396,726, issued Aug. 13, 1968 to Sarnoff; 3,712,301, issued Jan. 23, 1973 to Sarnoff; 3,882,863, issued May 13, 1975 to Sarnoff et al.; 4,031,893, issued Jun. 28, 1977 to Kaplan et al. However, these syringes are not designed, nor could they be effectively or safely used for injecting into the marrow sinuses of bones, nor do they prevent needles used in the procedures from being exposed so that there is a danger of accidental needle punctures in use of these syringes.

The present invention overcomes the drawbacks of the prior art by providing an interactive external defibrillation and vascular drug injection system comprising an expert system., thereby enabling the system to be operated by a first responder who is not a physician. The expert system of the present invention receives physiological input data from measuring devices attached to the patient, analyzes the data, and issues instructions to the operator regarding patient treatment, including defibrillation, cardioversion, and drug injection.

The present invention may also be used with a patient in need of emergency cardiac care who is conscious, breathing, or who has a pulse or a pacemaker.

SUMMARY OF THE INVENTION

The present invention provides an interactive external defibrillation and drug injection system for use by a human operator for treating cardiac conditions in a patient. The system of the present invention comprises a measuring device attachable to a patient and capable of measuring or recording a patient's electrocardiogram (ECG). The system further comprises a CPU connected to receive input signals from the measuring devices indicative of measurements taken by those devices. The CPU is capable of analyzing these measurements and is further capable of transmitting control signals. The CPU is capable of deriving the patient's heart rate and heart rhythm from the ECG. The CPU also comprises a communication system capable of communicating information and instructions in a manner perceivable by a human operator. The communication system is also capable of receiving and analyzing input from a human operator relating to the cardiological treatment and condition of a patient.

It is the intent of the present invention that the information and instructions communicated by the CPU will be consistent with updated versions of the American Heart Association's current "Guidelines for Cardiopulmonary Resuscitation and Emergency Cardiac Care Recommendations of the 1992 National Conference," as recently published in the Journal of the American Medical Association, Oct. 28, 1992, Vol. 268, No. 16, pp. 2171-2302 and periodic updates. These guidelines will hereinafter be referred to as the "AHA Guidelines for CPR/ECC." In addition to these guidelines, it is the intent of the present invention that the CPU will also communicate instructions regarding the use of intraosseous autoinjectors to inject drugs into a patient.

The system of the present invention further comprises at least two electrical leads connectable to a patient and capable of delivering a sufficient amount of electrical energy to a patient to cardiovert or defibrillate a patient's heart. The system further comprises an electrical source comprising a discharge outlet electrically connected to the electrical leads and a control signal input electrically connected to the CPU. The electrical source is capable of storing and discharging electrical energy through the leads in sufficient predetermined selectable quantities and at sufficient predetermined selectable rates to defibrillate or cardiovert a patient's heart in a manner consistent with selected control signals and instructions from the CPU.

The system of the present invention further comprises one or more intraosseous autoinjector devices, each containing a premeasured amount of a predetermined drug. Each autoinjector device also comprises one or more identifiers such that each autoinjector drug can be promptly identified by a human operator in response to an instruction from the CPU.

Through use of the autoinjector of the present invention, a device and method is provided for very rapid, automated, and safe infusion of fluid and drugs into the circulatory system, e.g., into bone marrow. The autoinjector of the present invention further provides a device and method that will automatically puncture a bone, place a needle into the marrow, and infuse fluid into the circulatory system via the marrow. The autoinjector of the present invention automatically covers the needle before and after use to prevent accidental needle punctures. This autoinjector can be used either with the sternum or the tibia. The autoinjector of the present invention reduces the anatomical variability of skin thickness by compressing the skin over the bone in use.

The autoinjector of the present invention also provides a device and method that imparts velocity to a needle and syringe component such that the momentum rapidly places the needle through the skin and bone and into the marrow. The needle of the autoinjector of the present invention is adapted for use with such an autoinjector. This needle also facilitates drug delivery into the marrow, yet prevents backflow of fluids out of the bone.

In a first aspect of the autoinjector of the present invention, the autoinjector has a main housing with a front end. There is a forward directed aperture on the front end of the main housing. A syringe body has a front end and a rear end. The syringe body is slidably positioned in the main housing. A needle has a central bore communicating with at least one opening proximate to a tip of the needle. The needle is attached to the front end of the syringe body, communicates with an interior of the syringe, and is positioned to extend through the aperture of the main housing. A drive plunger extends from the rear of the syringe body. A means on the main housing and engaging the drive plunger locks and unlocks the drive plunger in position at the rear end of the syringe body. A means is connected to the drive plunger for applying propelling force to the drive plunger to move the syringe body along the main housing in a first direction to extend the needle from the aperture when the device is pressed against a patient to expel the drug from the syringe body into the patient. A means is connected to the syringe body to move the syringe body in a second direction opposite to the first direction for withdrawing the needle into the aperture when the device is no longer pressed against a patient.

In a second aspect of the autoinjector of the present invention, a device for delivery of a drug in liquid to bone marrow comprising a main housing with a front end is provided. There is a forward directed aperture on the front end of the main housing. The syringe body of the present invention has a front end and a rear one° The syringe is slidably positioned in the main housing. A needle having a central bore communicating with at least one opening proximate to a tip of the needle is attached to the front end of the syringe body, communicates with an interior of the syringe body, and is positioned to extend through the aperture of the main housing in appropriate distance for passing through a patient's skin, penetrating a bone and entering the marrow inside the bone. A means imparts a force to the syringe body and to the needle, to extend the needle through the aperture of the main housing the appropriate distance at a sufficient velocity to pass through the patient's skin, penetrate the bone and enter the marrow. A means discharges the drug in liquid form from the autoinjector of the present invention through the needle and into the marrow.

In a third aspect of the autoinjector of the present invention, a needle for use in a device for delivery of a drug in liquid form with a taper along its length and a conical, orifice-free tip, is provided. A central bore communicates with a plurality of orifices proximate to the tip. The plurality of orifices are positioned circumferentially on the needle at different distances from the tip.

In a fourth aspect of the autoinjector of the present invention, a method for delivering a drug in liquid form to bone marrow includes positioning a syringe including a needle above a patient's skin at a location over a bone containing marrow. Sufficient velocity is imparted to the syringe so that the needle will have sufficient momentum to pass through the patient's skin, penetrate the bone and enter the marrow. The drug in liquid form is discharged from the syringe, through the needle and into the bone marrow.

BRIEF DESCRIPTION OF THE DRAWINGS

FIG. 1 is a cross-section view of a first embodiment of a device for rapid vascular drug delivery of the invention.

FIGS. 2-5 are similar cross-section views of the device of FIG. 1 at different stages in its use.

FIG. 6 is an external perspective view of a second embodiment of a device for rapid vascular drug delivery of the invention.

FIG. 7 is an exploded perspective view of the device of FIG. 6.

FIGS. 8-12 are cross-section views of a portion of the device of FIGS. 6-7.

FIG. 13 is an enlarged side view of a portion of the devices of FIGS. 1-12 in use.

DESCRIPTION OF THE PREFERRED EMBODIMENTS

Figure 14:
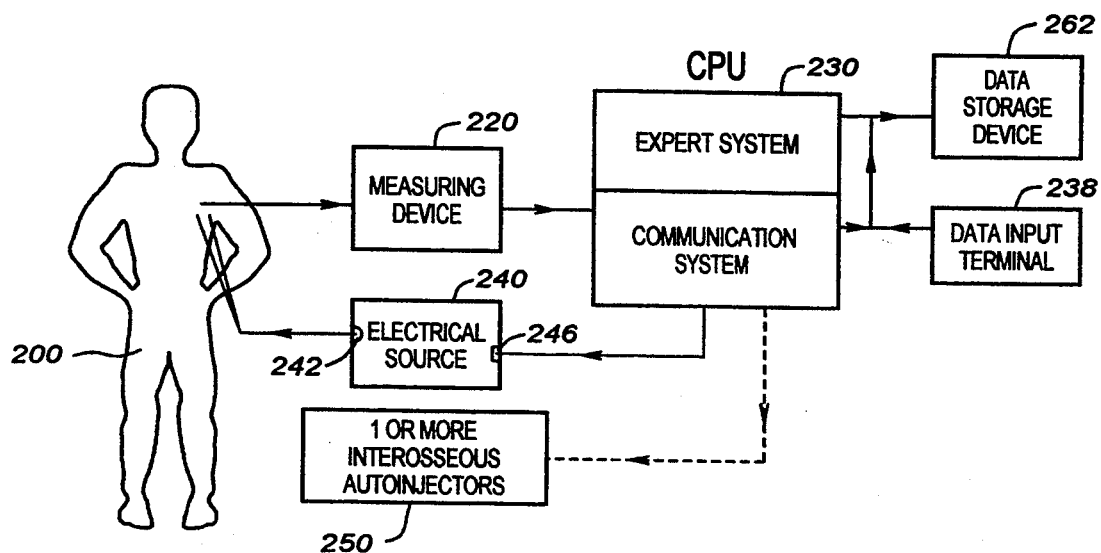
FIG. 14 is a block diagram of one embodiment of the present invention.

Turning now to the drawings, more particularly to FIG. 1, there is shown a an intraosseous autoinjector 10 for rapid vascular drug delivery. The intraosseous autoinjector 10 incorporates a cylindrical syringe body 12, fitted with a double side-holed pencil point needle 14. The syringe body is held in a cylindrical main housing 16 having a front barrel 18 with an orifice 20 through which the needle 14 may be extended. A cylindrical actuation handle 48 fits over end 24 of the main housing 16 for sliding movement along the main housing. A syringe plunger 26 contacts drive plunger 28 and extends into the syringe body 12 to confine liquid medication 32 in the syringe body 12. A main spring 34 extends between the drive plunger 28 and partition 36 on the actuation handle 48 to bias the actuation handle 48 in its extended position along the main housing 16 as shown in FIG. 1. A needle return spring 38 extends between the front barrel 18 and a collar 40 on the syringe body 12 to bias the needle to its retracted position as shown in FIG. 1. The main spring 34 exerts a stronger biasing force when compressed than the needle return spring 38. The drive plunger 28 has an annular peripheral socket 42 for one or more lock balls 44, which engage one or more openings 45 on the main housing 16 to lock the drive plunger in position with respect to the syringe body 12. A mating annular lock ball trip pocket 46 is positioned on inside surface of the actuation handle 48 to allow the intraosseous autoinjector 10 to be fired when the lock ball(s) in socket 42 reach the pocket 46. In FIG. 1, the intraosseous autoinjector 10 is shown in its uncocked position.

In use, the intraosseous autoinjector 10 is placed with the end of the front barrel 18 on the midline of the sternum at the second or third intercostal space, and then the intraosseous autoinjector 10 is pushed against the sternum. Compression of the spring 34 behind the syringe body 12 occurs as the front barrel 18 is pushed toward the actuation handle 48 and generates a force that will be used for needle 14 advancement and drug 32 injection. When an adequate force has been stored in the spring 34, the front barrel 18 has been pushed back to a point so that the lock ball(s) 44 are able to enter the trip pocket 46, as shown in FIG. 2. This entry releases the lock ball(s) 44, so that the main spring 34 is free to drive the syringe body 12 and the needle 14 forward with a force of approximately 25 to 40 pounds until collar 40 rests against ridge 50, as shown in FIG. 3.

The needle 14 is extended from about 8 mm to about 25 mm in order to ensure that side holes in the needle are in the marrow. The main spring 34 then pushes the syringe plunger 26 forward to the position shown in FIG. 4 to deliver the drug 32 through the extended needle 14 to the marrow in the sternum. Needle placement takes about 1/10th of a second, while drug delivery usually occurs in less than a second. Operation in this manner causes the syringe body 12 to reach a sufficient velocity so that the penetration of the needle 14 into the marrow occurs in a single, rapid, uninterrupted motion due to momentum of the syringe body 12 and needle 14. Relying on momentum in this manner means that a smaller diameter needle can be used than would be required if the penetration resulted from application of penetrating force on the needle while it was at rest against the skin or bone. Upon completion of drug delivery, the operator releases the pressure against the sternum, and the needle retraction spring 38 withdraws the needle 14 into the barrel 18 of the main housing 16 to the position shown in FIG. 5.

FIGS. 6–12 show another intraosseous autoinjector 100 for the rapid delivery of a drug to the marrow. The intraosseous autoinjector 100 incorporates a locking, cylindrical protective cover 102 over front barrel 104 to ensure that needle 14 is never exposed except when the intraosseous autoinjector 100 is both pressed against the patient's body and actuated. A cover return spring 106 is positioned between the protective cover 102 and shoulder 108 on cylindrical main housing 110 of the device. The protective cover 102 has an end 112 that extends into actuation handle 114 of the intraosseous autoinjector 100. End 112 is equipped with a tab locking mechanism 116 that, once actuated, prevents the protective cover 102 from being moved from its extended position as shown in FIG. 8 to its withdrawn position, against the barrel 104, as shown in FIG. 9. The locking mechanism 116 consists of two parts: a lock 118 circumferentially positioned around the end 112 between the protective cover 102 and the actuation handle 114, and a sleeve 120 concentrically positioned over the lock 118. The lock 118 has a plurality of spring tabs 122 extending rearward of the actuation handle 114 from a cylindrical base 124. The sleeve 120 has a plurality of projections 126, which are not springs, extending rearward beyond the tabs 122 from a similar cylindrical base 128. With the parts of the intraosseous autoinjector 100 in the positions shown in FIG. 8, prior to use of the intraosseous autoinjector 100, the cylindrical base 128 of the sleeve 120 rests over the spring fingers 122 of the lock 118, holding them down. A sealing membrane 134 is provided inside the barrel 104, over orifice 136, to protect the needle 14 prior to use of the device.

In use of the intraosseous autoinjector 100, with the spring fingers 122 in their down position, the protective cover 102 is free to retract against the barrel 104 to the position shown in FIG. 9, when the protective cover 102 is pressed downward against, e.g., the sternum or the tibia. As the protective cover 102 moves toward the barrel 104, the projections 126 of the sleeve 120 engage shoulder 130 of the actuating handle 114, so that the base 128 of the sleeve 120 is pushed down over the base 124 of the lock 118, allowing the spring fingers 122 of the lock 118 to spring outward, as shown in FIG. 9. Continued downward pressure of the intraosseous autoinjector 100 on the sternum or tibia moves the protective cover 102 and the barrel 104 into the actuating handle 114, as shown in FIG. 10, until the main body 108 and the actuating handle reach the firing position, as in the FIGS. 1–5 embodiment. At that time, firing occurs, the needle 14 is extended into the sternum or tibia, and the drug is ejected into the marrow through the needle 14, as shown in FIG. 11 in the same manner as in the FIGS. 1–5 embodiment. When the intraosseous autoinjector 100 is no longer pressed against the patient, the protective cover 102 is returned to its original position by the force of spring 106, as shown in FIG. 12. Because the spring tabs 122 have sprung outward, they engage shoulder 132, on the actuating handle, to lock the protective cover 102 over the needle 14. Thus, the needle is never exposed except when the intraosseous autoinjector 100 is actually pressed against the patient, and the needle 14 cannot be re-exposed after actuation, even if the device is again pressed against the patient or any object. In addition to the main spring 34, a secondary spring 138, separated from the main spring by member 140, is provided to ensure that there is still a spring force urging the needle 14 forward when it is fully extended. Except as shown and described, the construction and operation of the FIGS. 6–10 embodiment of the invention is the same as that of the FIGS. 1–5 embodiment.

FIG. 13 shows details of the needle 14 used in the devices 10 and 100. The needle 14 has a slight taper along its length toward a conical, orifice free tip 150. The taper promotes a good seal between the needle 14 and bone 156. The tip 150 of the needle 14 is free of an orifice because orifices located there would tend to clog during penetration of the bone 156. Orifices 158 are located behind the conical tip 150 and communicate with a central bore 160 extending the length of the needle to communicate with the reservoir of drug 32 (FIG. 1). The orifices 158 are staggered around the circumference of the needle 14 and connect to slits 162 extending vertically along the side of the needle. This configuration and placement of the orifices 158 and the slits 162 allow discharge of the drug 32 from an orifice 158, even if it is partially blocked by a tissue globule 164 in the marrow 166.

Examples of drugs that can be life saving for specific medical and cardiac emergencies if administered into the circulation in a timely manner, and hence, candidates for packaging in the devices 10 and 100, are shown in the following table:

| DRUG | MEDICAL EMERGENCY |
| --- | --- |
| Adenosine | Symptomatic Paroxysmal Supra Ventricular Tachycardia (PSVT) |

-continued

| DRUG | MEDICAL EMERGENCY |
| --- | --- |
| Aminophylline | Asthma, congestive heart failure (CHF) |
| Amrinone | CHF not associated with myocardial infarction (MI) |
| Atropine | Bradycardia, organophosphate poisoning, third degree heart block, asystole |
| Bretylium | Ventricular fibrillation |
| Bumetanide | CHF, pulmonary edema |
| Butorphanol | Moderate to severe pain |
| Calcium Chloride | Acute hyperkalemia, hypocalcemia |
| Chlorpromazine (Thorazine ®) | Acute psychotic episodes |
| Dexamethasone | Anaphylaxis |
| Diazepam (Valium ®) | Seizures |
| Diazoxide (Hyperstat ®) | Hypertensive emergency |
| Digoxin | CHF, atrial flutter/fibrillation |
| Diphenhydramine (Benadryl ®) | Anaphylaxis |
| Dobutamine | CHF |
| Dopamine | Cardiogenic shock, hypovolemic shock |
| Edrophonium | Cardiac arrest, shock, anaphylaxis, etc. |
| Esmolol | Symptomatic supraventricular tachycardia |
| Furosemide | CHF, pulmonary edema |
| Glucagon | Hypoglycemia |
| Haloperidol (Haldol ®) | Acute psychotic episodes |
| Hydralazine | Hypertiesive emergency |
| Hydrocortisone | Severe anaphylaxis |
| Insulin | Diabetic ketoacidosis |
| Isoproterenol | Bradycardias |
| Labetalol | Hypertensive crisis |
| Lidocaine | Ventricular arrhythmias, MI |
| Magnesium sulfate | Eclampsia |
| Mannitol | Acute cerebral edema, blood transfusion reactions |
| Meperidine (Demerol ®) | Severe pain |
| Metaraminol | Cardiogenic shock |
| Methylprednisolone | Severe anaphylaxis |
| Metoprolol (Lopressor ®) | Acute MI |
| Morphine | Severe pain, pulmonary edema |
| Nalbuphine | Moderate to severe pain |
| Naloxone (Narcan ®) | Narcotic overdose, coma |
| Norepinephrine (Levophed ®) | Hypotension, neurogenic shock |
| Oxytocin | Postpartum vaginal bleeding |
| Phenobarbitol | Seizures, acute anxiety |
| Phenytoin (Dillantin ®) | Major seizures |
| Physostigmine | Tricyclic overdose, belladonna or atropine overdose |
| Pralidoxime (2-PAM, Protopam ®) | Organophosphate poisoning |
| Procainamide | Ventricular arrhythmias |
| Promethazine (Phenergan ®) | Nausea and vomiting |
| Propanolol (Inderal ®) | Cardiac arrhythmias |
| Sodium Bicarbonate | Cardiac arrest, antidepressant overdose |
| Sodium Nitroprusside | Hypertensive emergency |
| Succinylcholine | To induce paralysis |
| Thiamine (vitamin B1) | Coma, alcoholism, delirium tremors |
| Verapamil | PSVT |

Many of the above medical emergencies are and can be life threatening. The vascular delivery of the above drugs can be life saving. Even a few seconds delay in therapy can be a matter of life or death in a medical emergency. The intraosseous autoinjector of the present invention can be used to administer these drugs into the central circulation, often in less than 1 or 2 seconds. The administration of drugs in this manner can be safely and effectively performed by a lay person with minimal training and, overall, offers a safe, effective, and extremely rapid means to treat medical emergencies.

Because momentum is used to advance the needle through the cortical bone and into the marrow, even a small gauge needle, such as a 20 to 25 gauge simple pencil-point with side holes, could be properly placed. Because the effective dose of most of the previously listed drugs could be carried in exceedingly small volumes, such as 0.1 to 0.2 ml or less, such a small gauged needle could be used for rapid drug delivery. Alternatively, a larger needle (12 to 18 gauge), either a simple pencil-point or the design previously described, could be used to administer rapidly 1.0 to 5.0 ml of fluid. The invention and these needles can be used to effectively deliver drugs into circulation in as short a time as 1 to 2 seconds or less.

While the intraosseous autoinjector of the present invention has been shown in two preferred forms, various modifications of it could be made. For example, the device could be construed so that it is cocked or loaded prior to placing it in contact with the patient, and merely fired after it is pressed against the patient with a suitable pressure. The devices 10 and 100 have been shown and described as configured for IO infusion. The same principle of an automatic syringe that is automatically spring loaded for injection by pressing against the patient could be adapted to an automatic syringe for subcutaneous or intramuscular injection as well.

The intraosseous autoinjector of the present invention punctures a bone containing marrow, places a needle into the marrow, and infuses fluid into the circulatory system via the marrow. The device covers the needle before and after use to prevent accidental needle punctures.

Figure 15:
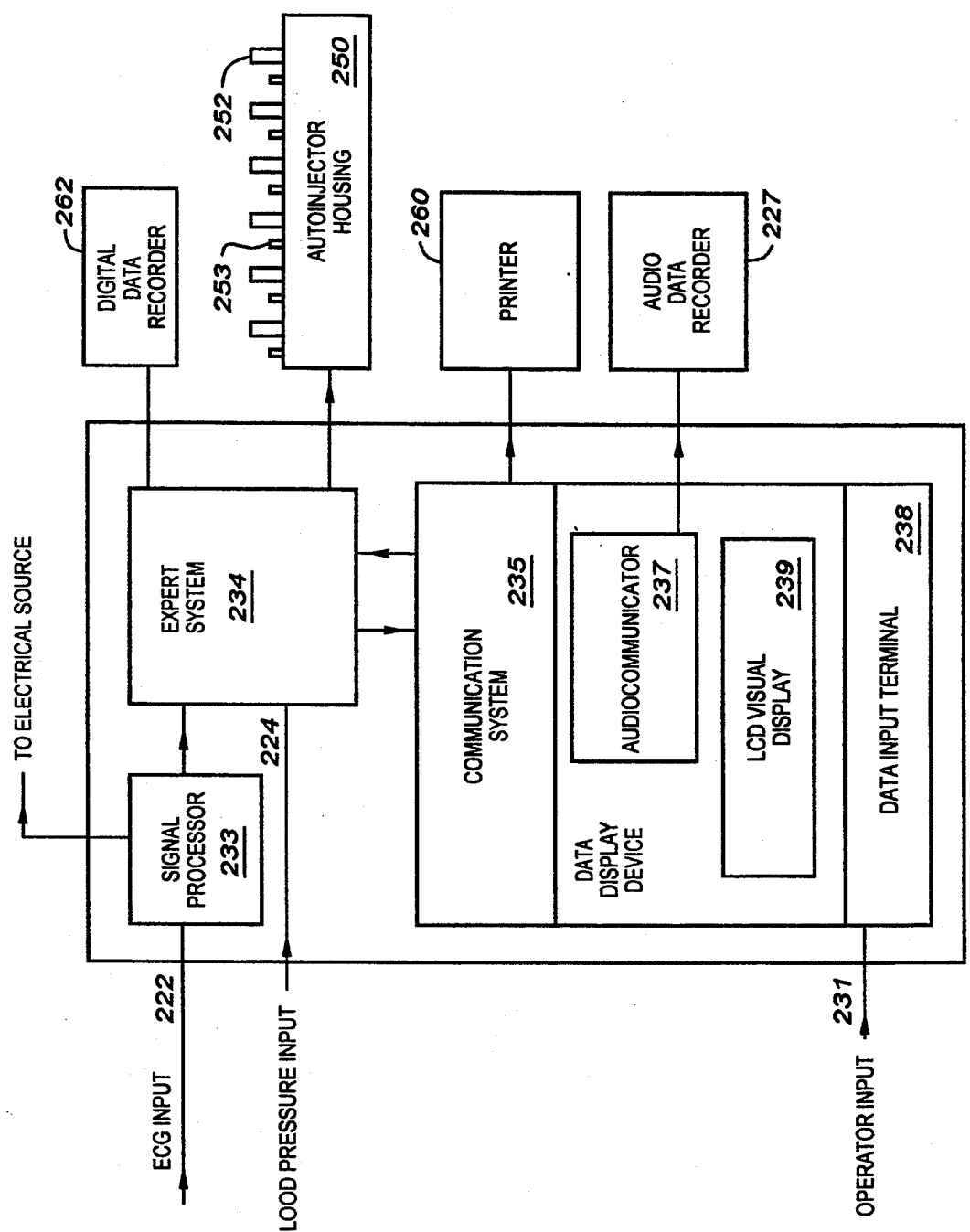
FIG. 15 is a more detailed illustration of the internal configuration of the CPU of the present invention.

A block diagram of an interactive external defibrillation and drug injection system for use by a human operator for treating cardiac conditions or other medical emergencies in a patient is shown in FIG. 14. A measuring device 220 is attached to a patient 200. The measuring device is capable of measuring a patient's ECG. In a preferred embodiment, the measuring device is also capable of measuring a patient's blood pressure. A CPU 230 is connected to receive input signals from the measuring device indicative of measurements taken by the measuring device. As shown in FIG. 15, these input signals may include an ECG input 222 and a blood pressure input 224.

The CPU is capable of analyzing the measurements received from the measuring device and of transmitting control signals. In a preferred embodiment, the CPU comprises a programmable expert system 234 that is capable of analyzing measurements from the measuring devices to identify cardiac dysrhythmias, and a signal processor 233 capable of receiving an input signal indicative of a patient's ECG. The expert system is also capable of receiving ECG data from the signal processor and identifying the QRS complex and the R wave. The expert system is further capable of analyzing inputs from the measuring devices to determine heart rate and heart rhythm, or to diagnose atrial contraction, or a ventricular contraction. The signal processor is further capable of transmitting a control signal to the electrical source. The dysrhythmias and conditions that the expert system is capable of identifying include ventricular fibrillation (VF), ventricular tachycardia (VT), acute myocardial infarction (MI), bradycardia, tachycardia, pulseless electrical activity (PEA), asystole, hypotension, shock, and acute pulmonary edema (APE).

In a preferred embodiment, the expert system comprises a multiplicity of cardiological treatment and diagnostic algorithms capable of receiving input data from the measuring device and from a human operator, and further capable of Generating instructions to a human operator via the communication system 235. These algorithms are depicted in FIGS. 18A–18I. In the embodiment shown in FIG. 17, the buttons labeled "1" and "2" are intended for use by a qualified person, such as a medical director of an emergency medical services department, to program the expert system of the present invention. In a preferred embodiment the programming means is located in the back of the device in a compartment that is masked by a locked panel.

Figure 18A:
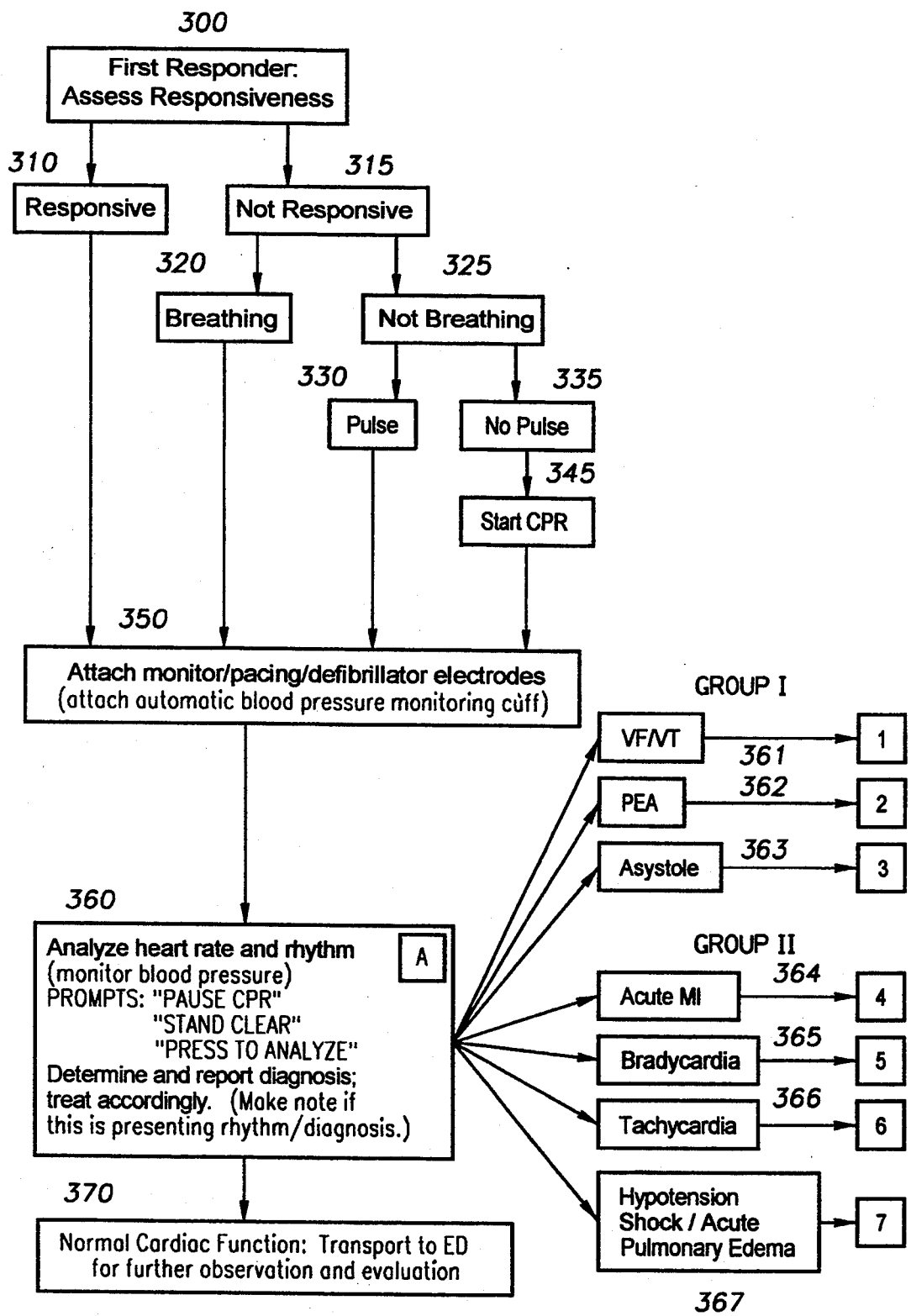
FIGS. 18A-18I, when taken together, constitute a flow chart of algorithms employed by the expert system of the present invention.

FIG. 18A is a block diagram depicting the scope of treatment and diagnostic algorithms encompassed by the expert system of the present invention. These algorithms may be modified to conform with the most current standards of CPR/ECC, as published by The American Heart Association in journals known in the art, such as the *Journal of the American Medical Association*. Additionally, some modifications to these algorithms may be programmed by the end user under the direction of qualified medical personnel, to reflect "standing orders" or standards of practice of CPR/ECC of an end user EMS system.

The interactive nature of this expert system is illustrated by block 300, depicting an assessment of a patient's responsiveness by a first respondence and by block 360 depicting various instructions or prompts Generated by the expert system to the first responder regarding treatment to be administered to a patient. The assessments depicted by blocks 315–345 in FIG. 18A, reflect action that a first responder would be trained to take without the assistance of an expert system. Block 350 depicts the attachment of measuring devices of the present invention such that the expert system can perform the analysis and provide the instructions depicted in block 360. The various dysrhythmias that may be diagnosed by the expert system are depicted at blocks 361–367 of FIG. 18A. Each of these dysrhythmias is shown in greater detail in FIGS. 18B–18I.

Figure 18B:
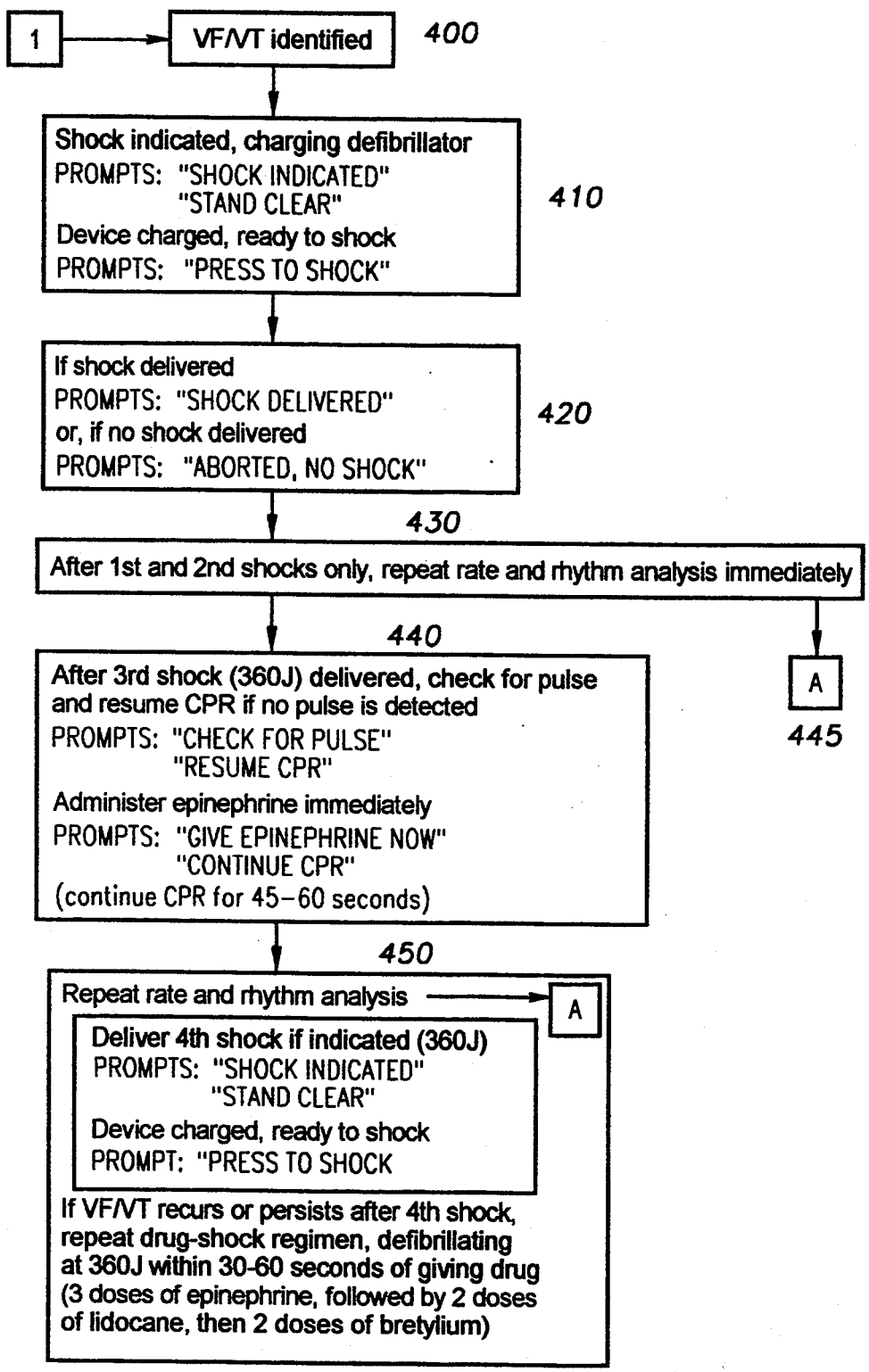

FIG. 18B depicts the general algorithm for use in treating VF and VT. The interactive nature of the present invention is illustrated by the prompts and instructions shown at blocks 410, 420, 440, and 450. These instructions encompass the use of electrical shocks, as well as the administration of drugs. It is the intent of the present invention that where instructions to administer drugs, such as those shown in blocks 440 and 450 are given, the first responder would administer such drugs using the autoinjectors of the present invention. The instruction depicted by block 445 is an instruction to perform the analysis depicted at block 360 at FIG. 18A.

Figure 18C:
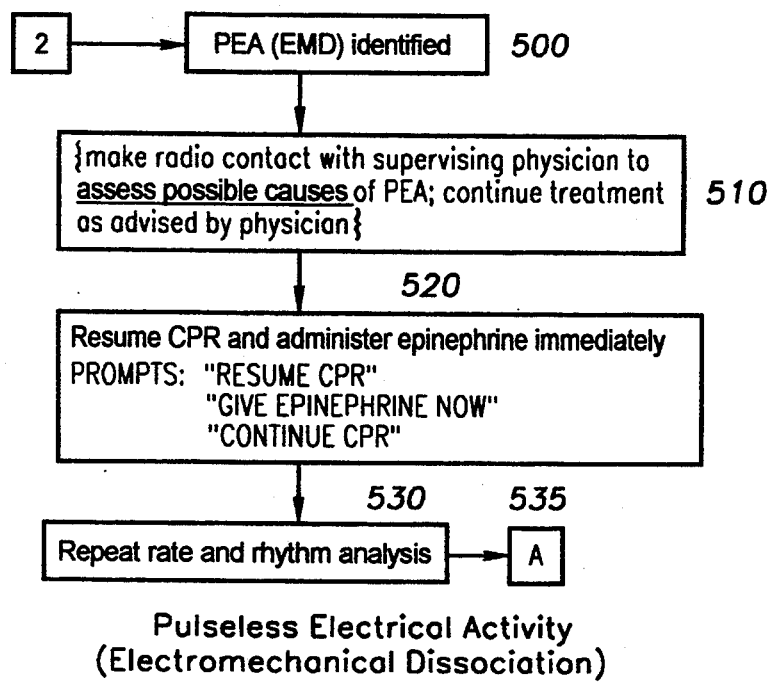

The algorithm of the expert system for the treatment of PEA is shown in FIG. 18C. PEA is also known as electromechanical dissociation to those of ordinary skill in the cardiological art. Block 520 illustrates an instruction from the expert system to administer a drug using the autoinjector, as well as CPR.

Figure 18D:
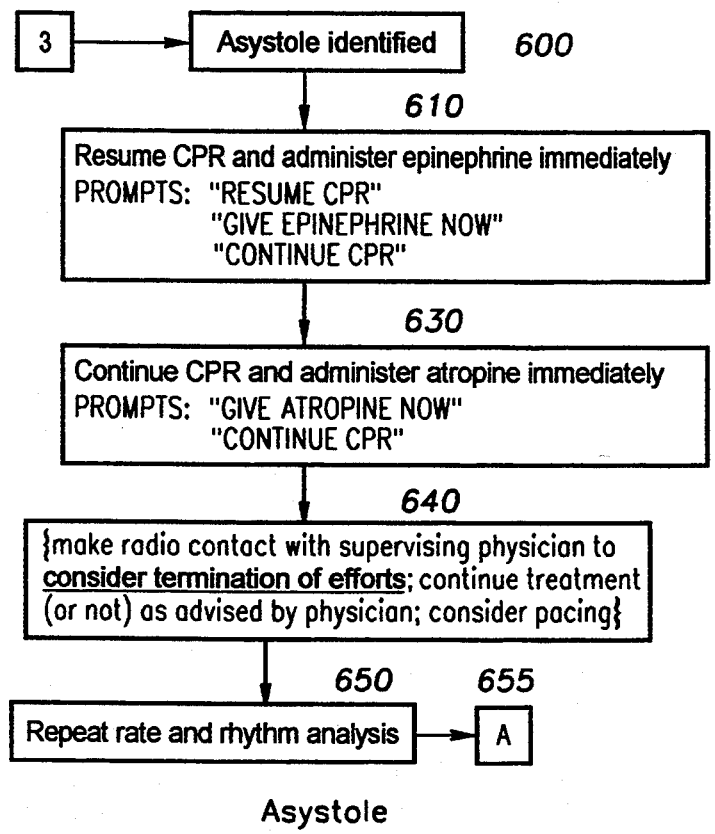

The algorithm of the expert system for the treatment of asystole is illustrated in FIG. 18D. Block 620 and 630 illustrate instructions from the expert system to administer drugs to a patient using the autoinjector. Block 650 and 655 instruct the operator to perform the analysis shown in block 360 of FIG. 18A.

Figure 18E:
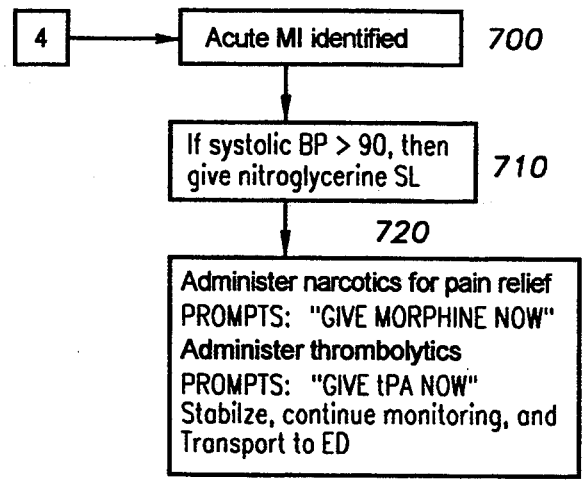

The algorithm of the expert system for the treatment for acute MI is illustrated in FIG. 18E. As shown in block 710, this algorithm utilizes blood pressure input 224, as also depicted in FIG. 15. Block 720 illustrates prompts from the CPU to the operator to administer drugs to a patient, using the autoinjectors of the present invention.

Figure 18F:
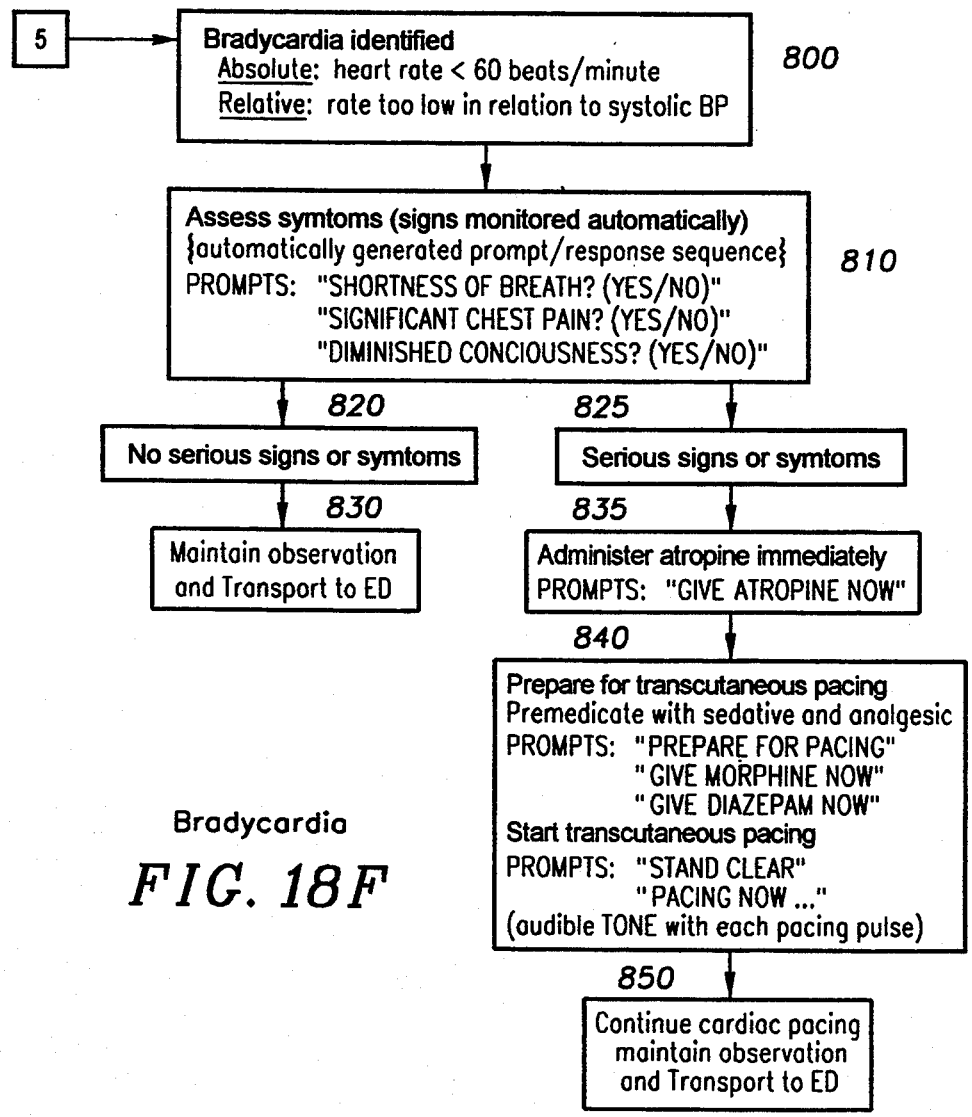

The algorithm of the expert system for the treatment of bradycardia is illustrated in FIG. 18F. As shown in block 800, this algorithm utilizes heart rate. In response to the prompts shown in block 810, it is the intent of the present invention that the operator would input data into the CPU using data input terminal 238 of FIG. 15. The expert system would then use this data to proceed with the algorithm, as shown in blocks 820–850.

Figure 18G:
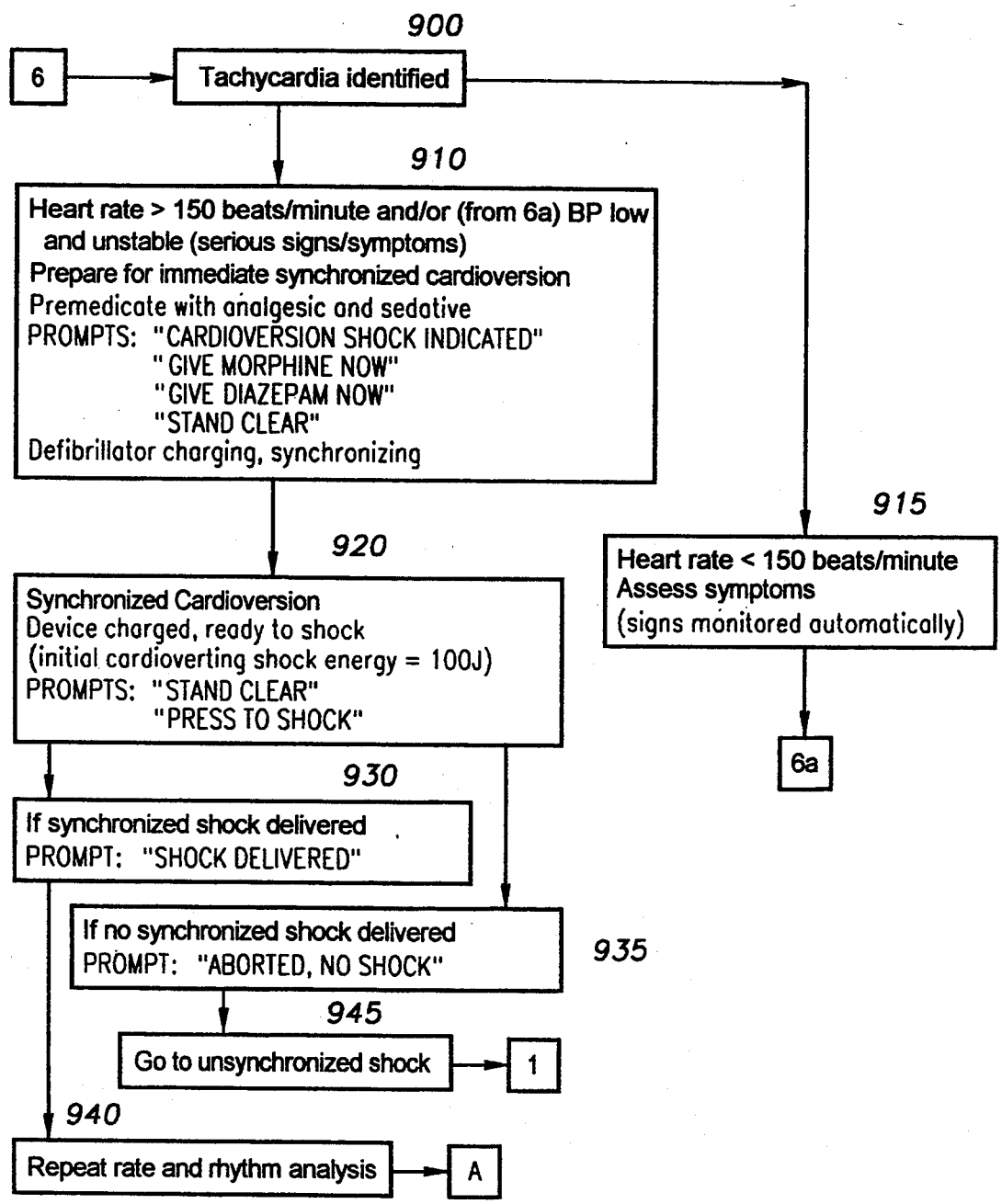

The algorithm of the expert system for the treatment of tachycardia where the heart rate of the patient is greater than 150 beats per minute, is illustrated in FIG. 18G. As shown in block 910, this algorithm utilizes heart rate input or blood pressure input 224, as also depicted in FIG. 15. The synchronized cardioversion referred to in block 920 is performed in conjunction with the output of a control signal from signal processor 233 to electrical source 240.

Figure 18H:
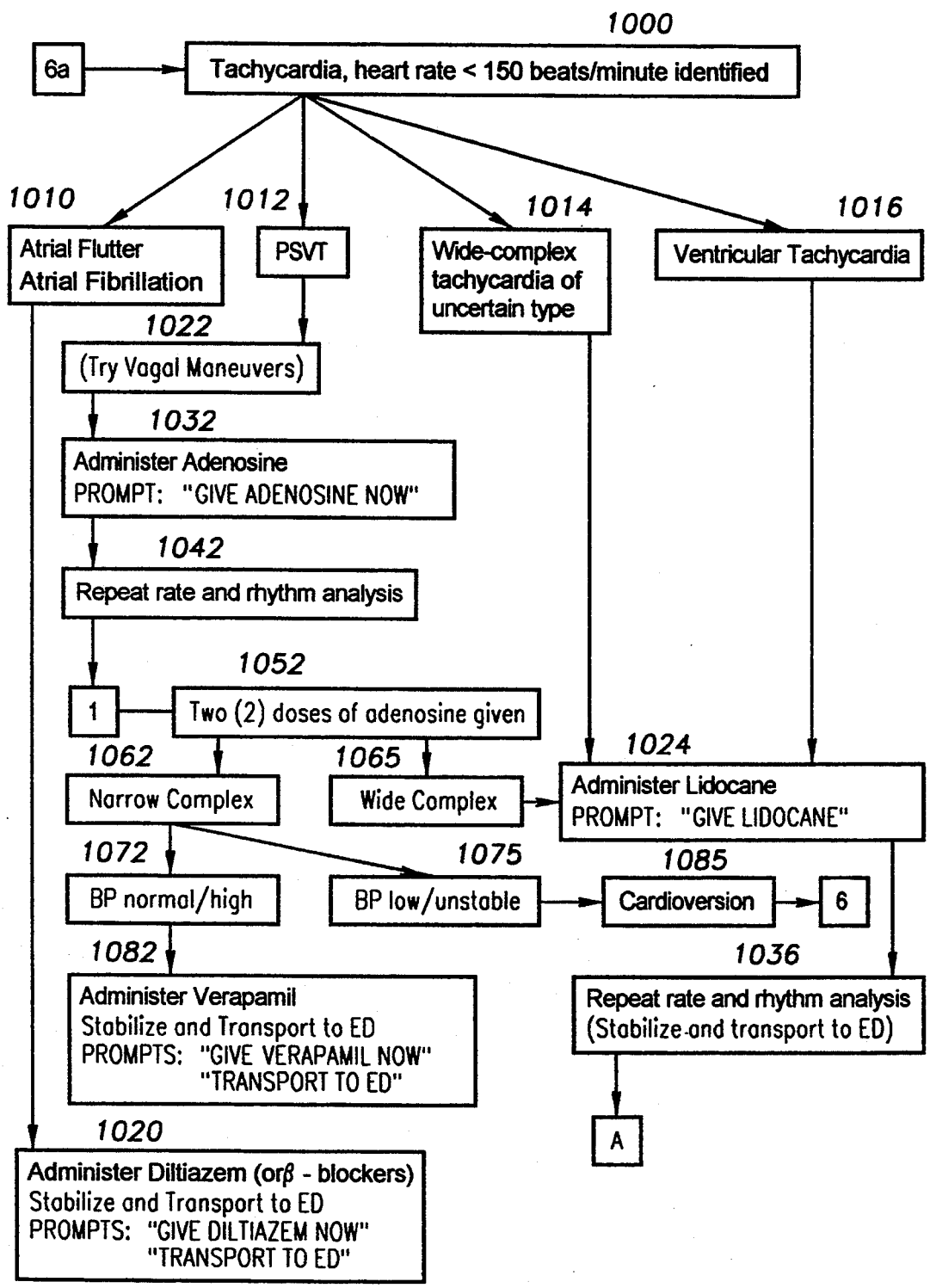

The algorithm of the expert system for the treatment of tachycardia where the heart rate of the patient is less than 150 beats per minute as measured by measuring devices 200 is illustrated in FIG. 18H. In contrast to treatment for tachycardia where the heart rate of the patient is greater than 150 beats per minute, treatment for tachycardia where the heart rate of the patient is less than 150 beats per minute, initially includes drugs rather than cardioversion.

Figure 18I:
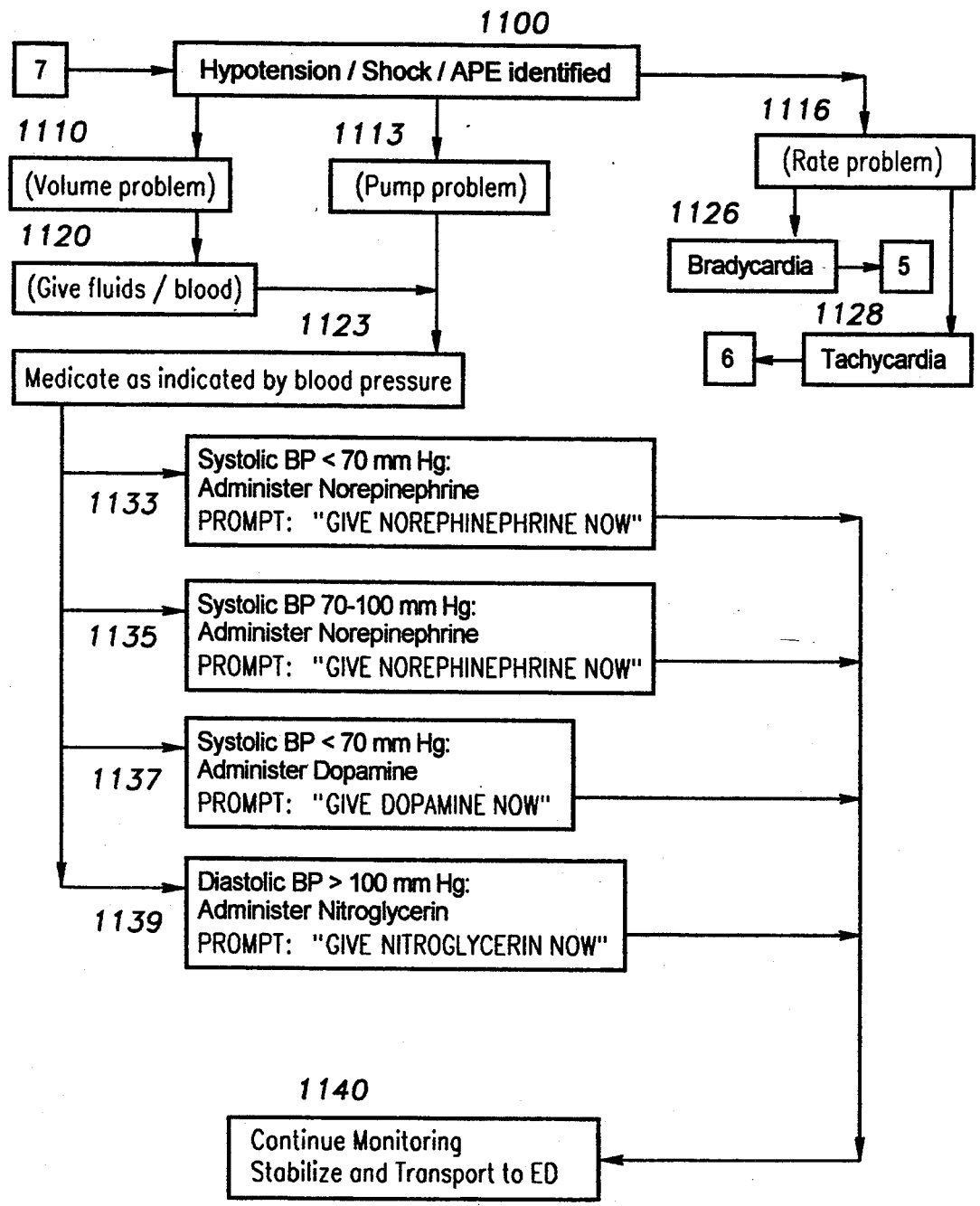

The algorithm of the expert system for the treatment of hypotension, shock, or acute pulmonary edema is illustrated by FIG. 18I. As shown in blocks 1133–1139, blood pressure input 224 is used by this algorithm to determine which drugs are to be administered by the autoinjectors.

Figure 17:
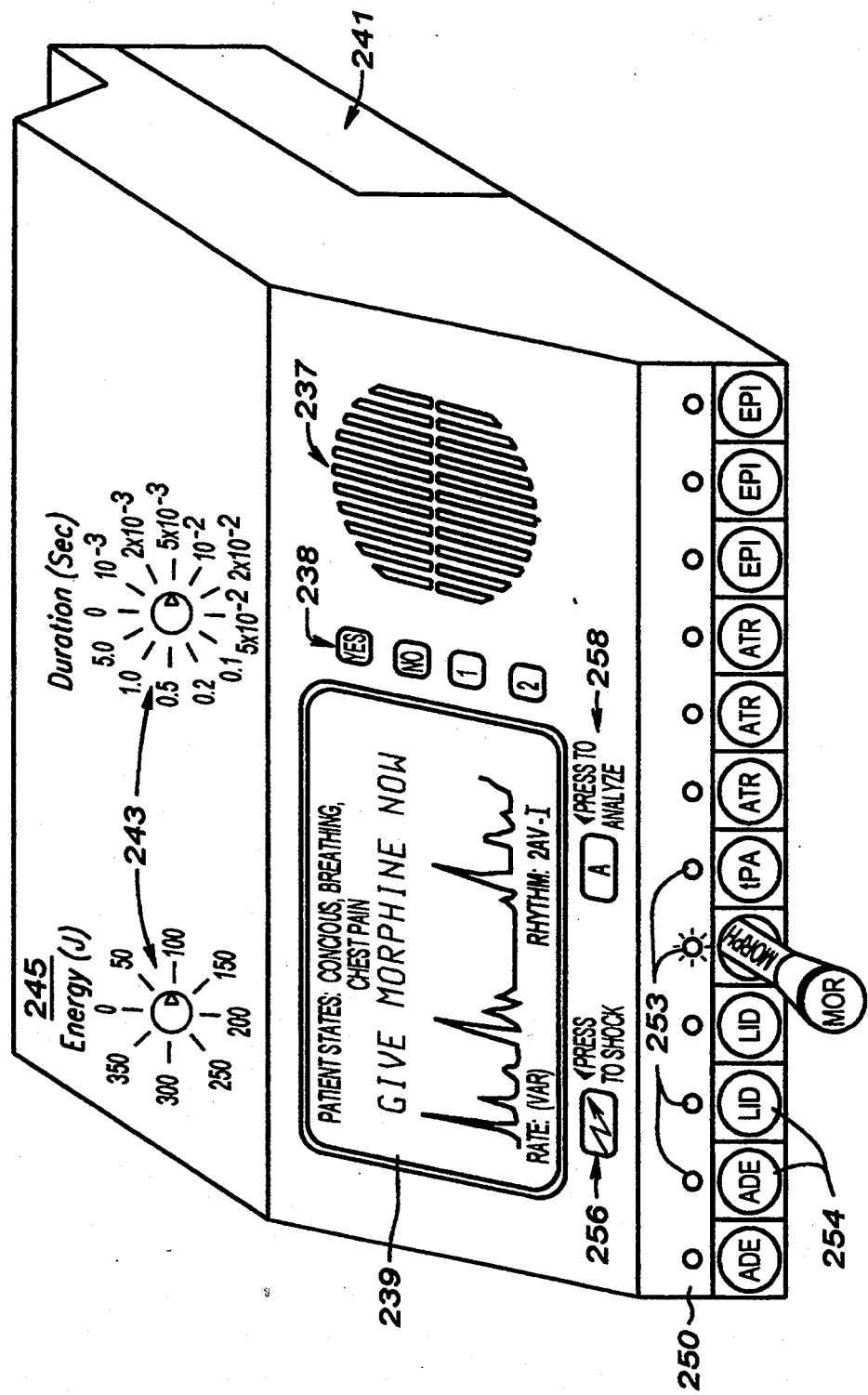
FIG. 17 is an isometric view of one embodiment of the present invention.

In a preferred embodiment, the communication system of the CPU comprises a data display device 236 capable of displaying data from the measuring device and instructions generated by the algorithms of the expert system, as shown in FIGS. 15 and 17. In a preferred embodiment, the data display device comprises an LCD visual display 239 and an audio communicator 237. Input from a human operator 231 is received via a data input terminal 238.

In a preferred embodiment, the data input terminal is a keyboard, or, alternatively, one or more buttons that can be pushed by a human operator to signal an affirmative or a negative response to an inquiry or "prompt" generated by the expert system. The buttons labeled "yes" and "no," 238 in FIG. 17, may be pushed by a human operator to indicate an affirmative or negative response, respectively, to a query generated by the CPU. The audio communicator is capable of communicating data and instructions to a human operator in an audibly perceivable manner.

In a preferred embodiment, the invention comprises a data storage device 262 that stores all data received by the CPU from the measuring devices or from an operator and all instructions and control signals generated by the CPU, as shown in FIG. 14. This data is stored in a retrievable fashion such that an operator can later determine what measurements and input were received by the CPU, as well as what instructions were given by the CPU. In a preferred embodiment, the data storage device further comprises a clock capable of storing the time at which all data was received by and all instructions were generated by the CPU, in a retrievable fashion.

The invention may further comprise an audio recorder 227, capable of recording audible events occurring near the CPU. Such events would include audio commands from the communication system of the CPU and statements made to and from the operator of the invention.

In a preferred embodiment, a printer 260 may be attached to the CPU such that any retrievably stored data in the CPU can be printed out on a "hard copy." In another embodiment of the present invention, the data storage device 262 is a digital data recorder 262, which is electrically coupled to the CPU, as shown in FIG. 15. In a preferred embodiment, the digital data recorder is automatically activated whenever the CPU is turned on. The digital data recorder records all signals transmitted by measuring devices to the CPU, all input from an operator to the CPU, all instructions generated by the CPU, and the times that all data inputs, operator inputs, control signals, and instructions were received or generated by the CPU, in a retrievable fashion.

The interactive external defibrillation and drug injection system of the present invention further comprises at least two electrical leads 244 connectable to a patient 200 and capable of delivering a sufficient amount of electrical energy to a patient to cardiovert or defibrillate a patient's heart. These leads may be repositioned on the patient, or an additional lead may be used, to confirm the presence of asystole. In a preferred embodiment, the present invention comprises more than two electrical leads. Such an embodiment is particularly useful when the operator wishes to diagnose MI.

The system of the present invention further comprises an electrical source 240 comprising a discharge outlet 242 electrically connected to the electrical leads. The electrical source further comprises a control signal input 246 electrically connected to the CPU. The electrical source is capable of storing and discharging electrical energy through the discharge outlet to the leads in sufficient predetermined selectable quantities and at sufficient predetermined selectable rates to defibrillate or cardiovert a patient's heart in a manner consistent with selected control signals and instructions from the CPU.

In a preferred embodiment, the electrical source is further capable of discharging electrical energy through the discharge outlet to the leads in sufficient predetermined selectable quantities and at sufficient predetermined selectable rates to transcutaneously pace a patient's heart in a manner consistent with selective control signals and instructions from the CPU. In this embodiment, the control signal generated by the CPU to regulate the transcutaneous pacing is indicative of the P wave, the QRS complex, the R wave, atrial contraction, and/or ventricular contraction of a patient's heart.

In one embodiment of the present invention, the electrical source and CPU are housed in a portable console 245 as shown in FIG. 17. In another embodiment, the electrical source and communication system are configured in a housing like that of the Heartstart® 3000 system.

In the preferred embodiment of FIG. 17, the electrical source further comprises a rechargeable battery 241 and a multiplicity of control devices 243 operable to permit a human operator to select the magnitude and duration of electrical energy discharged by the electrical source. Alternatively, this selection can be made by the expert system, and transmitted to the electrical source. The human operator would merely push button 256 on the console to deliver an electrical shock of the magnitude and duration selected by the expert system.

A console of the type shown in FIG. 17 may contain receptacles at its rear to receive leads from the measuring devices. In a preferred embodiment, this console would comprise at least three connections for three ECG leads. In another preferred embodiment, the console shown in FIG. 17 comprises an audio recorder, located at its rear. The audio recorder would automatically be activated anytime inputs are received by the CPU or instructions are generated by the CPU.

In the preferred embodiment shown in FIG. 17, the autoinjector housing 250 comprises a multiplicity of autoinjectors, including an autoinjector containing a premeasured amount of epinephrine (EPI), an autoinjector containing a premeasured amount of atropine (ATR), an autoinjector containing a premeasured amount of morphine (MOR), an autoinjector containing a premeasured amount of tissue plasminogen activator (tPA), an autoinjector containing a premeasured amount of lidocaine (LID), and an autoinjector containing a premeasured amount of adenosine (ADE). Each of these autoinjectors is an intraosseous autoinjector. The embodiment of the invention shown in FIG. 17 shows the preferred number of autoinjectors containing each drug.

The system of the present invention further comprises at least one intraosseous autoinjector which contains a premeasured amount of a predetermined drug. Each autoinjector device comprises an identifier, such that it can be promptly identified by a human operator in response to an instruction from the CPU. In a preferred embodiment, each autoinjector is removably housed in a portable autoinjector housing 250 comprising a visual labeling system 254 such that the drug contained within each autoinjector is readily perceivable by a human operator.

It is envisioned that the present invention is particularly applicable to pre-hospital or out-of-hospital treatment of a patient experiencing a cardiac emergency. When such a patient is delivered to a hospital or to the care of a person more highly trained than a first responder, such as a paramedic or a physician, it is particularly important for the paramedic or physician to known what drugs have been administered to the patient. The autoinjector housing embodiment of the present invention provides a means for a paramedic or other professional to readily ascertain what drugs have been administered from the number and color of empty autoinjector receptacles in the housing, as well as from a printout of all data and first responder or operator inputs recorded by the CPU.

In one embodiment of the present invention, the portable autoinjector housing is electrically coupled to the CPU, as shown in FIG. 15, such that it can receive a signal from the CPU indicative of which drug to administer to a patient. In this embodiment of the present invention, an electrical light 253 is situated in close proximity to each autoinjector and electrically connected to the CPU such that each light may be selectively illuminated by the CPU pursuant to instructions from the expert system to visually indicate which drug should be administered to a patient, as shown in FIG. 17. In one embodiment, these lights may be LEDs. These lights may be electrically coupled to the CPU such that they blink to indicate that an autoinjector should be used to administer drugs to a patient and they remain illuminated to indicate that an autoinjector has already been used to administer drugs.

In another embodiment of the present: invention, each autoinjector may be a unique color indicative of the drug it contains. In this embodiment, the unique color associated with each drug is programmed into the expert system such that the expert system can issue instructions regarding drug injection that identify a particular autoinjector by its color. This embodiment is not preferred when the operator is color blind; however, color coding may be used in conjunction with other forms of autoinjector identification, such as the electrical lights, described above, in order to provide redundant means of autoinjector identification.

Figure 16:
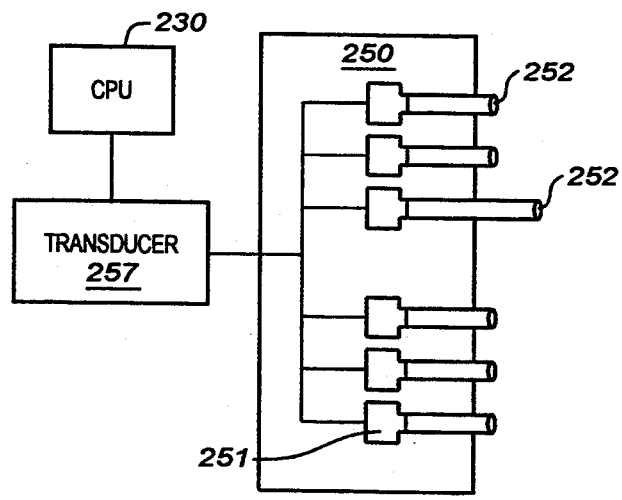
FIG. 16 is a block diagram of one embodiment of the autoinjector housing of the present invention.

In yet another embodiment, the autoinjector housing comprises a multiplicity of extendable jacks 251. One extendable jack is installed in each compartment, directly adjacent an autoinjector, as shown in FIG. 16. Each jack is mechanically coupled to a transducer 257 that is electrically coupled to the CPU such that each transducer can receive an extension signal for a specific autoinjector from the CPU, and transmit the signal to a specific jack, causing it to telescopically extend, thereby extending the adjacent autoinjector to a more prominent position relative to the other autoinjectors in the autoinjector housing. This extension provides a visual signal to a human operator to remove the extended autoinjector from the housing and administer the drug contained within that autoinjector to a patient.

In this embodiment, the CPU memory records which jack was actuated, the time it was actuated and the particular drug contained within the autoinjector stored adjacent that Jack. The CPU is also capable of providing prompts from its visual display in conjunction with the operation of the jack, instructing a human operator to remove the autoinjector that has been extended by operation of the jack. In this embodiment, the CPU would send inquiries to the human operator asking him to verify whether he has administered the drug contained within the extended autoinjector to a patient. The CPU memory would be capable of retrievably storing a human operator's answer and the time of the answer to such an inquiry.

Many modifications and variations may be made in the embodiments described herein and depicted in the accompanying drawings without departing from the concept of the present invention. Accordingly, it is clearly understood that the embodiments described and illustrated herein are illustrative only and are not intended as a limitation upon the scope of the present invention.

What is claimed is:

1. An interactive external defibrillation and drug injection system for use by a human operator for treating cardiac conditions or medical emergencies in a patient, comprising:
   (a) a measuring device attachable to a patient and capable of measuring a patient's ECG;
   (b) a CPU connected to receive input signals from said measuring device indicative of measurements taken by said measuring device, said CPU being further capable of analyzing said measurements and of transmitting control signals, and said CPU comprising a communication system capable of communicating information and instructions in a manner perceivable by a human operator and capable of receiving and analyzing data input by a human operator relating to the cardiological treatment and condition of a patient;
   (c) at least two electrical leads connectable to a patient and capable of delivering a sufficient amount of electrical energy to a patient to cardiovert or defibrillate a patient's heart;
   (d) an electrical source comprising a discharge outlet electrically connected to said electrical leads and a control signal input electrically connected to said CPU, said source capable of storing and discharging electrical energy through the discharge outlet to said leads in sufficient predetermined selectable quantities and at sufficient predetermined selectable rates to defibrillate or cardiovert a patient's heart in a manner consistent with selected control signals and instructions from said CPU; and
   (e) at least one intraosseous autoinjector, each of said autoinjectors containing a premeasured amount of a predetermined drug and each of said autoinjectors comprising an identifier such that it can be promptly identified by a human operator in response to an instruction from said CPU.

2. The interactive external defibrillation and drug injection system of claim 1, wherein said measuring device is further capable of measuring a patient's blood pressure.

3. The interactive external defibrillation and drug injection system of claim 2, wherein said CPU comprises:
   (a) a programmable expert system that is capable of analyzing measurements from said measuring device to identify cardiac dysrhythmias, heart rate, and heart rhythm; and (b) a signal processor capable of receiving an input signal indicative of a patient's ECG, processing said signal and transmitting a control signal to said electrical source.

4. The interactive external defibrillation and drug injection system of claim 3, wherein the cardiac dysrhythmias that are identifiable by said programmable expert system include ventricular defibrillation, ventricular tachycardia, acute myocardial infarction, bradycardia, tachycardia, pulseless electrical activity, asystole, and acute pulmonary edema.

5. The interactive external defibrillation and drug injection system of claim 3, wherein said expert system comprises a multiplicity of cardiological treatment and diagnostic algorithms capable of receiving input data from said measuring device and from a human operator, and further capable of generating instructions to a human operator via said communication system.

6. The interactive external defibrillation and drug injection system of claim 1, wherein said communication system further comprises a data display device capable of displaying data received from said measuring device and instructions generated by said algorithms.

7. The interactive external defibrillation and drug injection system of claim 5, further comprising a data storage device electrically coupled to said CPU, said storage device being capable of storing all data received by the CPU and all instructions and control signals generated by said CPU.

8. The interactive external defibrillation and drug injection system of claim 1, wherein said communication system further comprises an audio communicator capable of communicating data and instructions to a human operator in an audibly perceivable manner.

9. The interactive external defibrillation and drug injection system of claim 6, wherein said communication system further comprises a data input terminal capable of receiving data input by a human operator and transmitting such data to said algorithms.

10. The interactive external defibrillation and drug injection system of claim 3, wherein said electrical source is further capable of discharging electrical energy through the discharge outlet to said leads in sufficient predetermined selectable quantities and at sufficient predetermined selectable rates to transcutaneously pace a patient's heart in a manner consistent with control signals and instructions from the CPU.

11. The interactive external defibrillation and drug injection system of claim 1, wherein said electrical source and said CPU are housed in a portable console.

12. The interactive external defibrillation and drug injection system of claim 11, wherein said electrical source comprises:
(a) a rechargeable battery; and
(b) a multiplicity of control devices operable to permit a human operator to select the magnitude and duration of electrical energy discharged by said source.

13. The interactive external defibrillation and drug injection system of claim 11, further comprising:
(a) an intraosseous autoinjector containing a premeasured amount of epinephrine;
(b) an intraosseous autoinjector containing a premeasured amount of atropine;
(c) an intraosseous autoinjector containing a premeasured amount of morphine;
(d) an intraosseous autoinjector containing a premeasured amount of tissue plasminogen activator;
(e) an intraosseous autoinjector containing a premeasured amount of lidocaine; and
(f) an intraosseous autoinjector containing a premeasured amount of adenosine.

14. The interactive external defibrillation and drug injection system of claim 13, wherein each of said autoinjectors is removably housed in a portable autoinjector housing comprising a visual labeling system such that the drug contained within each autoinjector is readily perceivable by a human operator.

15. The interactive external defibrillation and drug injection system of claim 14, further comprising:
(a) a multiplicity of extendable jacks, each of said jacks installed in said autoinjector housing directly adjacent an autoinjector such that when said jack is extended, it extends the autoinjector directly above it into a more prominent position than that of the remaining autoinjectors in said housing; and
(b) a transducer electrically coupled to said CPU and mechanically coupled to said jacks such that said transducer can receive an extension signal for a specific autoinjector from said CPU and transmit said signal to the jack installed adjacent said selected autoinjector, resulting in the extension of said jack.

16. The interactive external defibrillation and drug injection system of claim 14, wherein said portable autoinjector housing is electrically coupled to said CPU such that it can receive a signal from said CPU indicative of which drug to administer to a patient.

17. The interactive external defibrillation and drug injection system of claim 16, further comprising an electrical light in close proximity to each of said autoinjectors, each of said lights being electrically connected to said CPU such that each light may be selectively illuminated by the CPU pursuant to instructions from the expert system to visually indicate which drug should be administered to a patient.

18. An interactive external defibrillation and drug injection system for use by a human operator for treating cardiac conditions in a patient, comprising:
(a) a measuring device attachable to a patient and capable of measuring a patient's ECG and blood pressure;
(b) a CPU connected to receive input signals from said measuring device indicative of measurements taken by said measuring device, said CPU being further capable of analyzing said measurements and of transmitting control signals, and said CPU comprising a communication system capable of communicating information and instructions in a manner perceivable by a human operator and capable of receiving and analyzing data input by a human operator relating to the cardiological treatment and condition of a patient;
(c) at least two electrical leads connectable to a patient and capable of delivering a sufficient amount of electrical energy to a patient to cardiovert, defibrillate, or transcutaneously pace a patient's heart;
(d) an electrical source comprising a discharge outlet electrically connected to said electrical leads and a control signal input electrically connected to said CPU, said source capable of storing and discharging electrical energy through the discharge outlet to said leads in sufficient predetermined selectable quantities and at sufficient rates to defibrillate, cardiovert, or transcutaneously pace a patient's heart in a manner consistent with selected control signals and instructions from said CPU, said source further comprising a multiplicity of control devices for use in selectively controlling the magnitude and duration of electrical energy discharged by said source; and (e) a portable container comprising at least six intraosseous autoinjectors, each of said autoinjectors containing a premeasured amount of a predetermined drug, said container further comprising an electrical light in close proximity to each of said autoinjectors, each of said lights being electrically connected to said CPU such that each light is illuminated in response to a signal from said CPU.

19. The interactive external defibrillation and drug injection system of claim 18, wherein said CPU comprises a programmable expert system that is capable of analyzing measurements from said measuring devices to identify heart rate, heart rhythm, and cardiac dysrhythmias.

20. The interactive external defibrillation and drug injection system of claim 18, further comprising a data storage device capable of storing all data and other input received by said CPU and all instructions and control signals generated by said CPU in a retrievable fashion such that an operator can determine the time at which all data received by said CPU was received and all instructions generated by said CPU were generated.

21. The interactive external defibrillation and drug injection system of claim 20, further comprising a printer electrically coupled to said CPU such that any retrievably stored data in said CPU can be printed out by said printer.

22. The interactive external defibrillation and drug injection system of claim 18, further comprising a digital data recorder electrically coupled to said CPU such that it can retrievably record all signals transmitted by measuring devices to the CPU, all input from an operator input to the CPU, all instructions generated by the CPU and the times that all such recorded data was received or generated by the CPU.

23. The interactive external defibrillation and drug injection system of claim 18, wherein said measuring device comprises:

(a) at least two ECG leads connectable to a patient and capable of transmitting a signal indicative of the patient's ECG; and (b) a blood pressure monitoring device.

24. The interactive external defibrillation and drug injection system of claim 18, wherein each of said autoinjectors comprise:

(a) a main housing having a front end and a rear end;

(b) a forward directed aperture on the front end of said main housing;

(c) a syringe body having a front end and a rear end, said syringe body being slidably positioned in said main housing;

(d) a needle having a central bore communicating with at least one opening proximate to a tip of said needle, said needle being attached to the front end of said syringe body, communicating with an interior of said syringe body and being positioned to extend through the aperture of said main housing;

(e) an actuation handle extending in telescoping fashion over the rear end of said main housing;

(f) a drive plunger extending from the rear ends of said syringe body and said main housing into said actuation handle;

(g) a drive spring capable of exerting and extending force between said drive plunger and said actuation handle;

(h) a needle return spring connected between the front end of said main housing for engaging said drive plunger in position at the rear end of said syringe body; and (i) a means placed on the front end of said main housing for locking said drive plunger into position and for unlocking said drive plunger from the rear end of said syringe body, causing said needle to be releasably extended from the front end of said main housing.

25. The interactive external defibrillation and drug injection system of claim 24, wherein said autoinjector further comprises a protective covering having a front end and a rear end, said protective covering being positioned over the front end of said main housing, the front end of said protective cover extending beyond the front end of said main housing at least a distance equal to the distance said needle extends through the aperture of said main housing when said device is operated, said protective cover having a corresponding aperture to the aperture of said main housing, the rear end of said protective cover extending into said actuation handle, said protective cover being initially movable rearward along said main housing in telescoping fashion over the front end of said main housing and a locking mechanism on said protective cover for preventing said protective cover from being moved rearward along said main housing again, after initially being moved rearward along said main housing.

* * * * *